(12) United States Patent
Grosman et al.

(10) Patent No.: US 12,133,969 B2
(45) Date of Patent: Nov. 5, 2024

(54) TRANSLATING THERAPY PARAMETERS OF AN INSULIN THERAPY SYSTEM TO TRANSLATED THERAPY PARAMETERS FOR USE AT A DIFFERENT INSULIN THERAPY SYSTEM

(71) Applicant: MEDTRONIC MINIMED, INC., Northridge, CA (US)

(72) Inventors: Benyamin Grosman, West Hills, CA (US); Yuxiang Zhong, Arcadia, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 939 days.

(21) Appl. No.: 17/118,519

(22) Filed: Dec. 10, 2020

(65) Prior Publication Data

US 2021/0178067 A1   Jun. 17, 2021

Related U.S. Application Data

(60) Provisional application No. 62/947,988, filed on Dec. 13, 2019.

(51) Int. Cl.
*A61M 5/172* (2006.01)
*G06F 3/01* (2006.01)
(Continued)

(52) U.S. Cl.
CPC .......... *A61M 5/1723* (2013.01); *G06F 3/017* (2013.01); *G16H 20/17* (2018.01); *G16H 40/40* (2018.01);
(Continued)

(58) Field of Classification Search
CPC ........ A61M 5/1723; A61M 2005/1401; A61M 2005/14288; A61M 2205/35;
(Continued)

(56) References Cited

U.S. PATENT DOCUMENTS 4,562,751 A   1/1986 Nason et al.
4,685,903 A   8/1987 Cable et al.
(Continued)

OTHER PUBLICATIONS

International Preliminary Report on Patentability dated Jun. 23, 2022, in PCT Application No. PCT/US2020/064693.
(Continued)

*Primary Examiner* — Jason E Flick
(74) *Attorney, Agent, or Firm* — Weaver Austin Villeneuve & Sampson LLP

(57) ABSTRACT

Systems, storage media and computer-readable media are provided for translating one or more therapy parameters of a first insulin therapy system to one or more translated therapy parameters for use at a second insulin therapy system that is different than the first insulin therapy system. A therapy profile generated at the first insulin therapy system can be send to a translation service. The therapy profile includes one or more therapy parameters. At least one therapy parameter from the therapy profile can be translated into at least one translated therapy parameter that is mapped to and adapted for use by the second insulin therapy system. The at least one translated therapy parameter can then be sent to the second insulin therapy system for use at the second insulin therapy system.

22 Claims, 15 Drawing Sheets

(51) Int. Cl.
*G16H 20/17* (2018.01)
*G16H 40/40* (2018.01)
*A61M 5/14* (2006.01)
*A61M 5/142* (2006.01)

(52) U.S. Cl.
CPC .............. *A61M 2005/1401* (2013.01); *A61M 2005/14288* (2013.01); *A61M 2205/3303* (2013.01); *A61M 2205/35* (2013.01); *A61M 2230/201* (2013.01)

(58) Field of Classification Search
CPC .. A61M 2230/201; A61M 2005/14208; A61M 5/168; A61M 2230/20; A61M 2230/00; A61M 2205/33; A61M 2005/14292; A61M 2005/14296; G16H 20/17; G16H 40/40; G16H 40/60; G16H 20/00; G16H 20/10; G16H 50/50
See application file for complete search history.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,771,251 B2 * | 7/2014 | Ruchti ................. G16H 20/17 604/67 |
| 2007/0123819 A1 | 5/2007 | Mernoe et al. |
| 2010/0160861 A1 | 6/2010 | Causey, III et al. |
| 2013/0274183 A1 | 10/2013 | Kim et al. |
| 2017/0351842 A1 | 12/2017 | Booth et al. |
| 2020/0135320 A1 | 4/2020 | Vleugels |
| 2020/0289373 A1 | 9/2020 | Vleugels |
| 2021/0178068 A1 | 6/2021 | Miller et al. |

OTHER PUBLICATIONS

International Search Report and Written Opinion dated Mar. 18, 2021, in Application No. PCT/US2020/064693.
U.S. Non-Final office Action dated Jan. 17, 2023 in U.S. Appl. No. 17/119,618.
Karl-Georg Petersen, A New Sortware for Initiating and Optimising Insulin Treatment of Out-Patients, Computer Methods and Programs in Biomedicine, 32 (1990), pp. 325-331, Department of Endocrinology, University Hospital of Internal Medicine, Freiburg, F.R.G.

* cited by examiner

TRANSLATING THERAPY PARAMETERS OF AN INSULIN THERAPY SYSTEM TO TRANSLATED THERAPY PARAMETERS FOR USE AT A DIFFERENT INSULIN THERAPY SYSTEM

CROSS-REFERENCE TO RELATED APPLICATION

This application claims the benefit of U.S. provisional patent application No. 62/947,988, filed Dec. 13, 2019.

TECHNICAL FIELD

The present technology is generally related to insulin therapy, and more particularly to systems, computer-readable storage media and methods for translating one or more therapy parameters of a first insulin therapy system to one or more translated therapy parameters for use at a second insulin therapy system.

BACKGROUND

Medical therapy delivery systems, such as fluid infusion devices, are relatively well known in the medical arts for use in delivering or dispensing an agent, such as insulin or another prescribed medication, to a patient. A typical medication infusion device includes a fluid pump mechanism and an associated drive system that actuates a plunger or piston of a fluid reservoir to deliver fluid medication from the reservoir to the body of a patient via a fluid delivery conduit between the reservoir and the body of a patient. Use of infusion pump therapy has been increasing, especially for delivering insulin to diabetic patients.

BRIEF SUMMARY

The subject matter of this disclosure generally relates to translating one or more therapy parameters of a first insulin therapy system to one or more translated therapy parameters for use at a second insulin therapy system. The disclosed embodiments can simplify configuration of a discrete insulin therapy system using information (e.g., therapy parameters) provided from a continuous insulin therapy system, such as a sensor augmented insulin pump system. Conversely, the disclosed embodiments can simplify configuration of a continuous insulin therapy system using information (e.g., therapy parameters) provided from a discrete insulin therapy system, such as smart insulin pen system. The disclosed embodiments can speed up the process of determining therapy parameters by eliminating much of the "manual" configuration that is typically needed and save patients and health care providers time and effort. Health care providers can start with a much more accurate estimate of those therapy parameters, and do not have to go through the iterative process of estimating the optimal therapy parameters. The disclosed embodiments can also help to optimize outcomes for a particular user, and can also help to eliminate potential errors that can occur in determining optimal therapy parameters to be used. The disclosed embodiments can also help reduce the need for re-calibration as a patient's condition changes.

In one aspect, the present disclosure provides systems, methods and computer-readable media for translating one or more therapy parameters of a first insulin therapy system to one or more translated therapy parameters for use at a second insulin therapy system that is different than the first insulin therapy system. A therapy profile generated at the first insulin therapy system can be send to a translation service. The therapy profile includes one or more therapy parameters. At least one therapy parameter from the therapy profile can be translated into at least one translated therapy parameter that is mapped to and adapted for use by the second insulin therapy system. The at least one translated therapy parameter can then be sent to the second insulin therapy system for use at the second insulin therapy system.

In another aspect, the present disclosure provides systems, methods and computer-readable media for translating one or more therapy parameters of a first insulin therapy system to one or more translated therapy parameters for use at a second insulin therapy system. When an event associated with a user is detected, an insulin delivery profile for a first insulin therapy system can be determined during a period following the event. The insulin delivery profile includes one or more therapy parameters for the first insulin therapy system to provide insulin delivery in accordance with the insulin delivery profile during the period following the event. The detected event can be mapped to the insulin delivery profile, and the one or more therapy parameters can be mapped to one or more translated therapy parameters for the second insulin therapy system that provide insulin delivery in accordance with the insulin delivery profile and satisfy an insulin delivery demand associated with that event. The mapping of the event to the one or more translated therapy parameters can be stored in a database. When the event is subsequently detected, the one or more translated therapy parameters for the second insulin therapy system can be sent to the second insulin therapy system.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
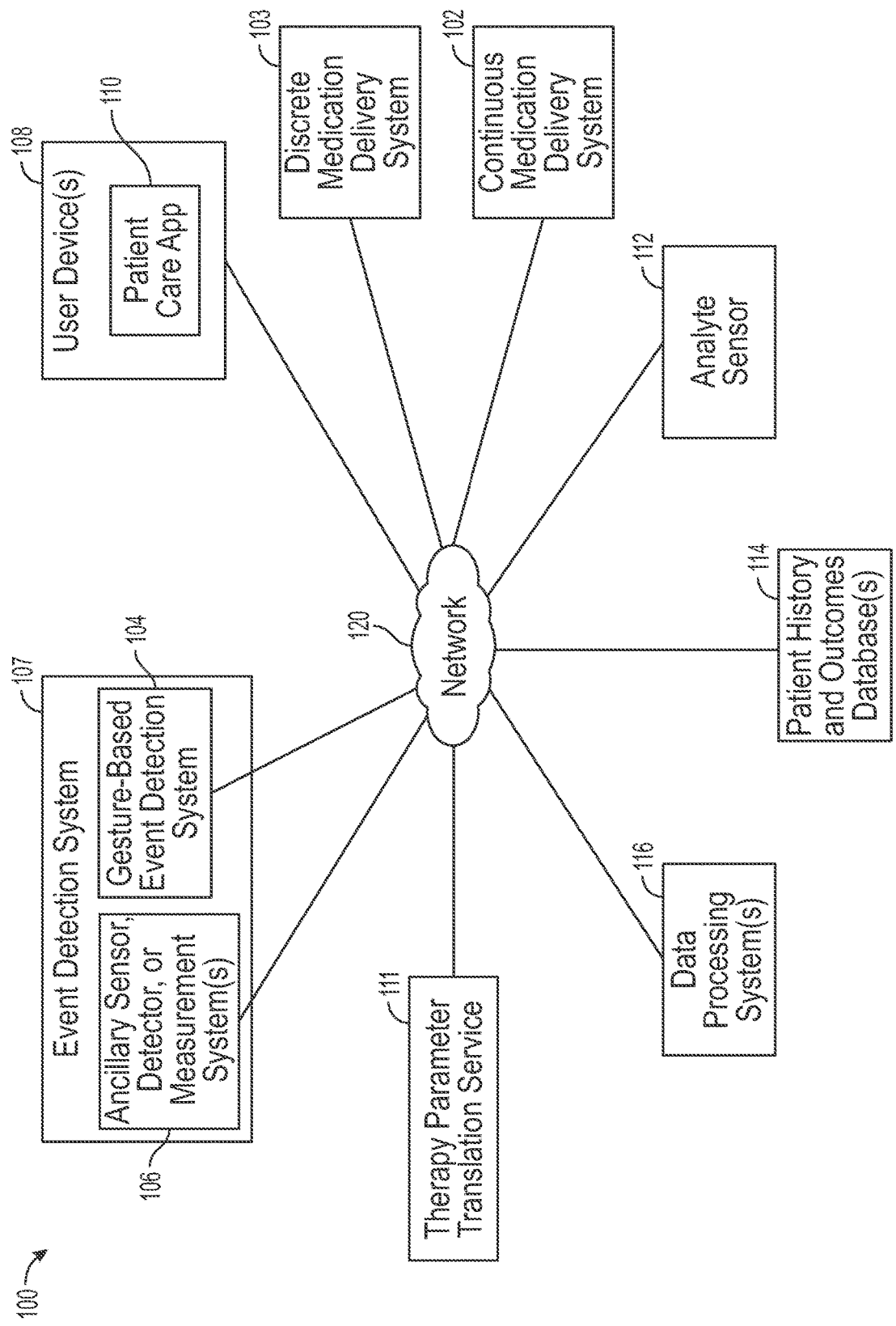
FIG. 1 is a simplified block diagram representation of an exemplary embodiment of a system that includes a medication delivery system that responds to changes in patient activity as indicated by the output of a gesture-based event detection system.

Control schemes have been developed to allow insulin infusion devices to monitor and regulate a patient's blood glucose level in a substantially continuous and autonomous manner. An insulin infusion device can be operated in an automatic mode wherein basal insulin is delivered at a rate that is automatically adjusted for the user. Moreover, an insulin infusion device can be operated to automatically calculate, recommend, and deliver insulin boluses as needed (e.g., to compensate for meals consumed by the user). Ideally, the amount of an insulin bolus should be accurately calculated and administered to maintain the user's blood glucose within the desired range. In particular, an automatically generated and delivered insulin bolus should safely manage the user's blood glucose level and keep it above a defined threshold level. To this end, an insulin infusion device operating in an automatic mode uses continuous glucose sensor data and control algorithms to regulate the user's blood glucose, based on a target glucose setpoint setting and user-initiated meal announcements that typically include estimations of the amount of carbohydrates to be consumed in an upcoming meal.

A continuous insulin therapy system, such as a sensor augmented insulin pump system continuously learns and customizes therapy parameters for a patient who is using the system. To use such a system, health care providers do not have to determine or set many therapy parameters.

By contrast, when a patient uses a discrete insulin therapy system, such as smart insulin pen system, a health care provider asks a patient basic questions to ascertain information about the patient, such as their body weight, time on insulin, age, and based on patient's answers provides some initial therapy parameters (e.g., insulin sensitivity factor, an insulin-to-carbohydrate ratio, active insulin time, etc.). Each time an insulin calculation is needed, the patient enters, at a user device, things like amount of carbohydrates they ate, their current blood glucose, etc. Based on information entered by the patient and the initial therapy parameters set by the health care provider, an application (e.g., running on the user device or server) then calculates a bolus estimate of insulin needed by the patient. After a time period of many months, the health care provider then evaluates how the original therapy parameters are working for the patient, and if changes are needed, the health care provider resets the therapy parameters.

This process of adjusting and optimizing therapy parameters can be time-consuming for the health care provider and patient. It involves a lot of trial and error to determine optimal therapy parameters used in conjunction with the discrete insulin therapy system. In addition, because a patient's condition can change depending on many factors like exercise, body weight, etc., it is often necessary to continuously re-calibrate the therapy parameters. It would be desirable to speed up the process of determining therapy parameters for a discrete insulin therapy system and optimizing their effectiveness for a particular patient.

In accordance with the disclosed embodiments, a system is provided in which a user temporarily uses a continuous insulin therapy system for a relatively short time period. The continuous insulin therapy system automatically determines and personalizes certain therapy parameters for the user, such as a basal profile comprising basal rate parameters and type and dosage of basal insulin; bolus data comprising type, dosage and timing of bolus insulin to meet insulin demand in response to the event; an active insulin time; an insulin sensitivity factor; an insulin-to-carbohydrate ratio, etc. These therapy parameters can then be extracted, translated into corresponding therapy parameters for a discrete insulin therapy system and used to calibrate the discrete insulin therapy system to provide a more accurate estimate of the therapy parameters thereby enabling the user to stop using the continuous insulin therapy system and use the discrete insulin therapy system. As such, a health care provider does not have to go through the iterative process of estimating the optimal therapy parameters for the discrete insulin therapy system and can start with a much more accurate estimate of those therapy parameters. At the same time, the user only needs to use the continuous insulin therapy system periodically to re-evaluate therapy parameters so that the health care provider can determine if adjustment of the discrete insulin therapy system is needed. As such, the disclosed embodiments can speed up the process of determining therapy parameters for a discrete insulin therapy system and optimize outcomes for a particular user. In addition, users who do not want to use a continuous insulin therapy system on a regular basis, for example, due to lifestyle and/or cost considerations, can more easily use a discrete insulin therapy system for their primary insulin therapy needs. For instance, this can be valuable to users such as travelers or athletes who only want to wear a continuous insulin therapy system periodically, and rely on a discrete insulin therapy system for their primary insulin therapy needs.

Transferring the therapy adjustments from a discrete insulin therapy system to a continuous insulin therapy system, or vice-versa can help provide beneficial therapy outcomes. For example, parameters such as the timing and dose of the long-acting insulin or the amount of injection needed to correct for high blood glucose can be set based on other system settings. The same transfer techniques can be applied to other settings, such as, a meal bolus. When well-established therapy adjustments are transferred after therapy regimens have been well establish transitions between devices can be safer and more effective. This can also reduce the time and/or number of clinical visits to a health care provider, and provide users/patients with better therapy. This can save same time and money in all aspects of a medical system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different arrangements than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Program code instructions may be configurable to be executed by one or more processors, such as one or more digital signal processors (DSPs), general purpose microprocessors, controllers, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

FIG. 1 is a simplified block diagram representation of an exemplary embodiment of a system 100 that responds to changes in the user's activity (e.g., eating, sleeping, exercise, and/or working habits) by regulating operation of a continuous medication delivery system 102 and/or a discrete medication delivery system 103 in an appropriate manner. In certain embodiments, the continuous medication delivery system 102 and/or the discrete medication delivery system 103 responds to changes in patient activity as indicated by the output of a gesture-based event detection system 104 and/or the output of at least one ancillary sensor, detector, or measurement system 106 (hereinafter referred to as ancillary system(s) 106). Certain embodiments of the system 100 include, without limitation: the continuous medication delivery system 102 that delivers medication to a user; the discrete medication delivery system 103 (or device) that delivers medication to a user; an event detection system 107 that includes at least one gesture-based event detection system 104 that monitors user behavior and/or status to obtain gesture data that indicates user activity events or behavior and at least one ancillary system 106; at least one user device 108 that includes or cooperates with a suitably written and configured patient care application 110; a parameter translation service or application 111; an analyte sensor 112 to measure a physiological characteristic of the user, such that sensor data obtained from the analyte sensor 112 can be used to control, regulate, configure or otherwise influence the operation of the continuous medication delivery system 102 and/or the discrete insulin therapy system 103; and at least one patient history and outcomes database 114. In accordance with certain cloud-implemented embodiments, the system includes at least one data processing system 116, which may be in communication with any or all of the other components of the system 100. Other configurations and topologies for the system 100 are also contemplated here, such as a system that includes additional intermediary, interface, or data repeating devices in the data path between a sending device and a receiving device.

As will be described in greater detail below, the parameter translation service (or app) 111 is provided for translating therapy parameters of the continuous insulin therapy system 102 to translated therapy parameters for use at the discrete insulin therapy system 103, and vice-versa. Depending on the embodiment, the parameter translation service 111 may be distributed across one or more different devices 102, 103, 104, 106, 108, 112, 114, 116 in the system 100 and the subject matter described herein is not limited to any particular implementation. Various embodiments of the parameter translation service 111 will be described in greater detail below with reference to FIGS. 9 through 16.

At least some of the components of the system 100 are communicatively coupled with one another to support data communication, signaling, and/or transmission of control commands as needed, via at least one communications network 120. The at least one communications network 120 may support wireless data communication and/or data communication using tangible data communication links. FIG. 1 depicts network communication links in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network can include or cooperate with any of the following, without limitation: a local area network; a wide area network; the Internet; a personal area network; a near-field data communication link; a cellular communication network; a satellite communication network; a video services or television broadcasting network; a network onboard a vehicle; or the like. The components of the system 100 may be suitably configured to support a variety of wireless and wired data communication protocols, technologies, and techniques as needed for compatibility with the at least one communication network 120.

The system 100 can support any type of continuous medication delivery system 102 and discrete medication delivery system 103 that is compatible with the features and functionality described here. The continuous medication delivery system 102 may be implemented as an electronic device that is operated to regulate the delivery of medication fluid to the user. In certain embodiments, the continuous medication delivery system 102 includes or is realized as an insulin infusion device, e.g., a portable patient-worn or patient-carried insulin pump or the like. The discrete medication delivery system 103 may be realized as a user-activated or user-actuated fluid delivery device, such as a manual syringe, an injection pen, a smart insulin pen, or the like. In some examples, the discrete medication delivery system 103 may include one or more applications running on a user device.

Both the continuous medication delivery system 102 and the discrete medication delivery system 103 can be utilized in conjunction with one or more analyte sensors. In such embodiments, the analyte sensor 112 includes or is realized as a glucose meter, a glucose sensor, or a continuous glucose monitor. For the sake of brevity, conventional techniques related to insulin infusion device operation, infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device (such as an insulin infusion device) includes a fluid pump mechanism having a motor or other actuation arrangement that is operable to linearly displace a plunger (or stopper) of a fluid reservoir provided within the fluid infusion device to deliver a dosage of fluid medication, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For a glucose control system suitable for use by diabetic patients, a closed-loop or automatic operating mode can be used to generate insulin dosage commands based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Figure 2:
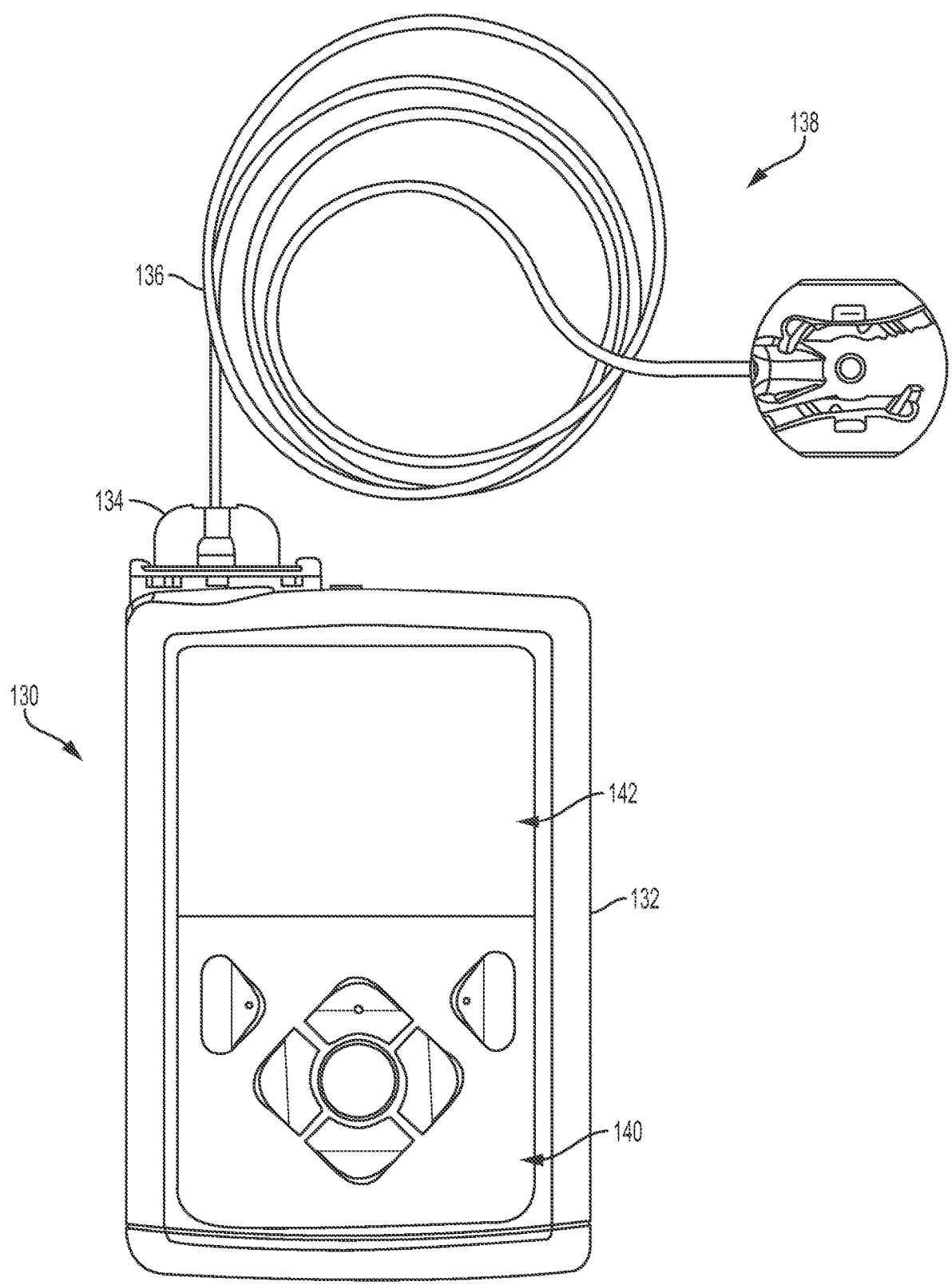
FIG. 2 is a plan view of an exemplary embodiment of an insulin infusion device that is suitable for use as the medication delivery system shown in FIG. 1.

FIG. 2 is a plan view of an exemplary embodiment of an insulin infusion device 130 suitable for use as the medication delivery system 102 shown in FIG. 1. The insulin infusion device 130 is a portable medical device designed to be carried or worn by the patient. The insulin infusion device 130 is one example of a device that can be used as part of the continuous medication delivery system 102 of FIG. 1. The insulin infusion device 130 can deliver insulin to a user without the need for manual injections. The insulin infusion device 130 can be part of a continuous insulin therapy system that includes one or more sensors such as a continuous glucose monitor. The insulin infusion device 130 can provide fast-acting insulin through a small tube placed under the skin, delivering two types of doses: basal or "background" insulin, which can be delivered continuously in tiny doses throughout the day and night; and bolus insulin to cover an increase in blood glucose from meals and/or to correct high blood glucose levels. The insulin infusion device 130 can provide insulin based on pre-programmed basal and bolus settings.

The illustrated embodiment of the insulin infusion device 130 includes a housing 132 adapted to receive an insulin-containing reservoir (hidden from view in FIG. 2). An opening in the housing 132 accommodates a fitting 134 (or cap) for the reservoir, with the fitting 134 being configured to mate or otherwise interface with tubing 136 of an infusion set 138 that provides a fluid path to/from the body of the user. In this manner, fluid communication from the interior of the insulin reservoir to the user is established via the tubing 136. The illustrated version of the insulin infusion device 130 includes a human-machine interface (HMI) 140 (or user interface) that includes elements that can be manipulated by the user to administer a bolus of fluid (e.g., insulin), to change therapy settings, to change user preferences, to select display features, and the like. The insulin infusion device 130 also includes a display 142, such as a liquid crystal display (LCD) or another suitable display technology, that can be used to present various types of information or data to the user, such as, without limitation: the current glucose level of the patient; the time; a graph or chart of the patient's glucose level versus time; device status indicators; etc. The insulin infusion device 130 may be configured and controlled to support other features and interactive functions described in more detail below.

Figure 3A:
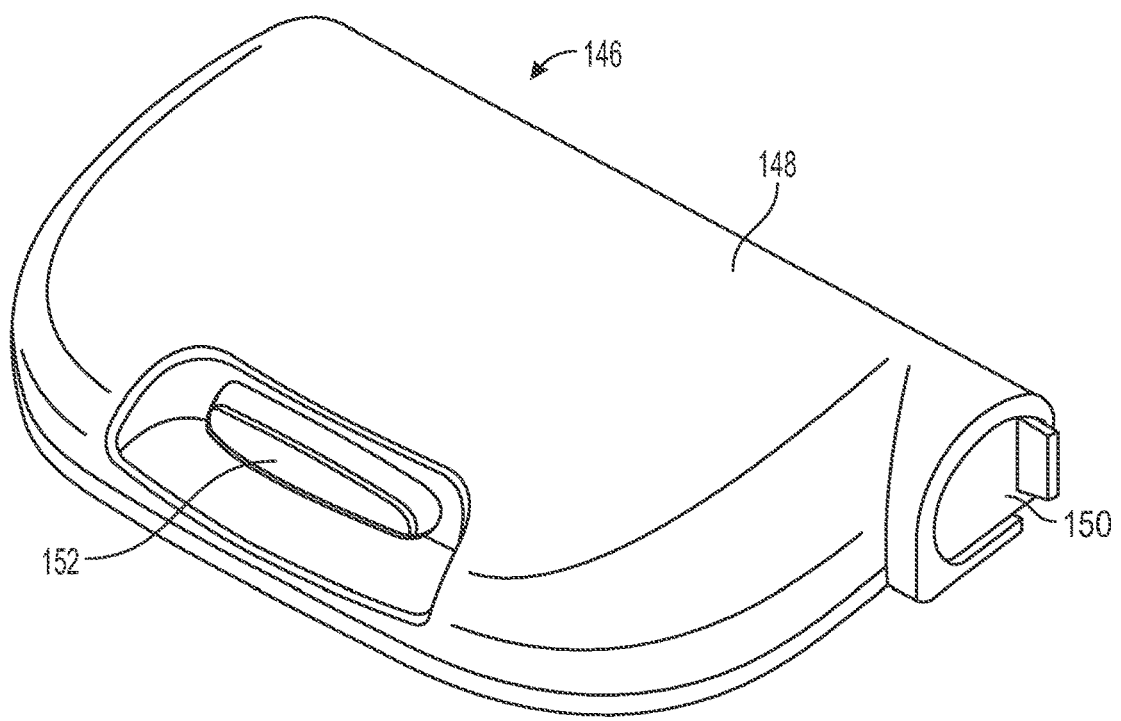
FIG. 3A is a top perspective view of an embodiment of an insulin infusion device implemented as a patch pump device that is suitable for use as the medication delivery system shown in FIG. 1.

FIG. 3A is a top perspective view of an embodiment of an insulin infusion device 146 implemented as a patch pump device that is suitable for use as the medication delivery system 102 shown in FIG. 1. The insulin infusion device 146 can be implemented as a combination device that includes an insertable insulin delivery cannula and an insertable glucose sensor (both of which are hidden from view in FIG. 3A). In such an implementation, the glucose sensor may take the place of the separate analyte sensor 112 shown in FIG. 1. The insulin infusion device 146 is another example of a device that can be used to implement the continuous medication delivery system 102 of FIG. 1. In this embodiment, the insulin infusion device 146 includes a housing 148 that serves as a shell for a variety of internal components. FIG. 3A shows the insulin infusion device 146 with a removable fluid cartridge 150 installed and secured therein. The housing 148 is suitably configured to receive, secure, and release the removable fluid cartridge 150. The insulin infusion device 146 includes at least one user interface feature, which can be actuated by the patient as needed. The illustrated embodiment of the insulin infusion device 146 includes a button 152 that is physically actuated. The button 152 can be a multipurpose user interface if so desired to make it easier for the user to operate the insulin infusion device 146. In this regard, the button 152 can be used in connection with one or more of the following functions, without limitation: waking up the processor and/or electronics of the insulin infusion device 146; triggering an insertion mechanism to insert a fluid delivery cannula and/or an analyte sensor into the subcutaneous space or similar region of the user; configuring one or more settings of the insulin infusion device 146; initiating delivery of medication fluid from the fluid cartridge 150; initiating a fluid priming operation; disabling alerts or alarms generated by the insulin infusion device 146; and the like. In lieu of the button 152, the insulin infusion device 146 can employ a slider mechanism, a pin, a lever, a switch, a touch-sensitive element, or the like. In certain embodiments, the insulin infusion device 146 may be configured and controlled to support other features and interactive functions described in more detail below.

Figure 3B:
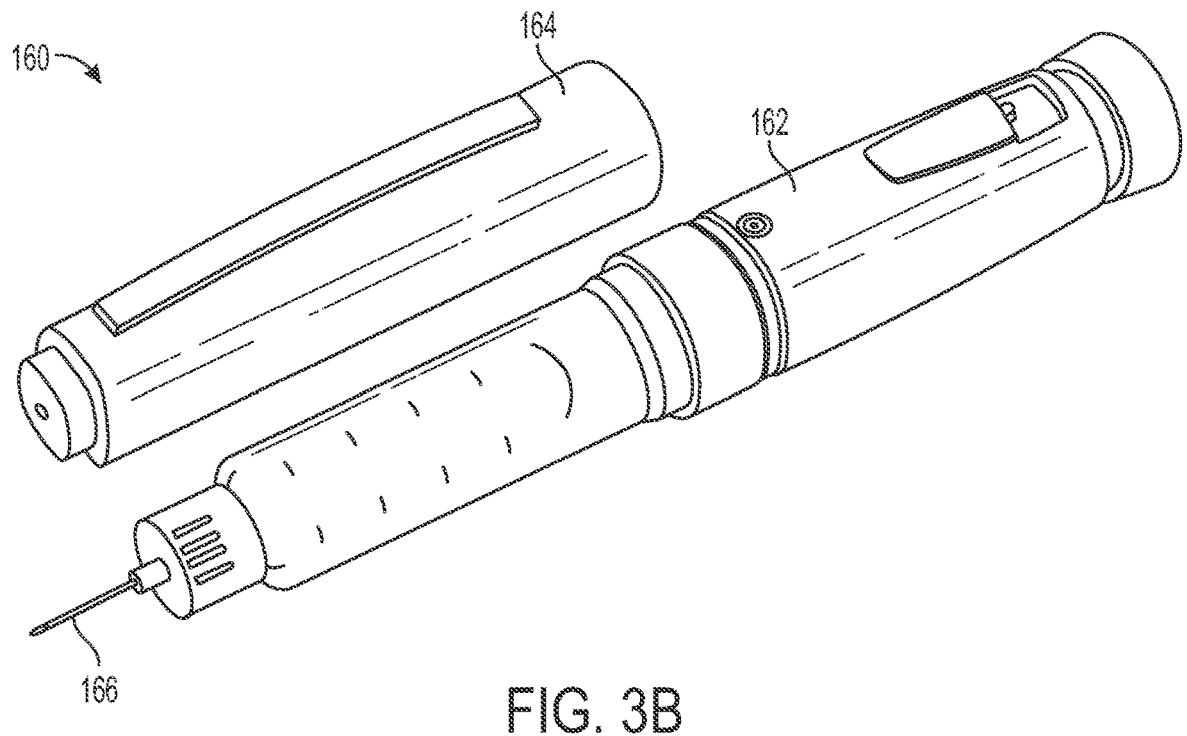
FIG. 3B is a perspective view of an exemplary embodiment of a smart insulin pen that is suitable for use as the medication delivery system shown in FIG. 1.

FIG. 3B is a perspective view of an exemplary embodiment of a smart insulin pen 160 suitable for use as the medication delivery system shown in FIG. 1. The smart insulin pen 160 is one example of a device that can be used as part of the discrete medication delivery system 103 of FIG. 1. The pen 160 includes an injector body 162 and a cap 164. FIG. 3B shows the cap 164 removed from the injector body 162, such that a delivery needle 166 is exposed. The pen 160 includes suitably configured electronics and processing capability to communicate with an application running on a user device, such as a smartphone, to support various functions and features such as: tracking active insulin; calculating insulin dosages (boluses); tracking insulin dosages; monitoring insulin supply levels; patient reminders and notifications; and patient status reporting. In certain embodiments, the smart insulin pen 160 can receive insulin dosage recommendations or instructions and/or recommended dosing times (or a recommended dosing schedule). Moreover, the smart insulin pen 160 may be configured and controlled to support other features and interactive functions described in more detail below.

Figure 4:
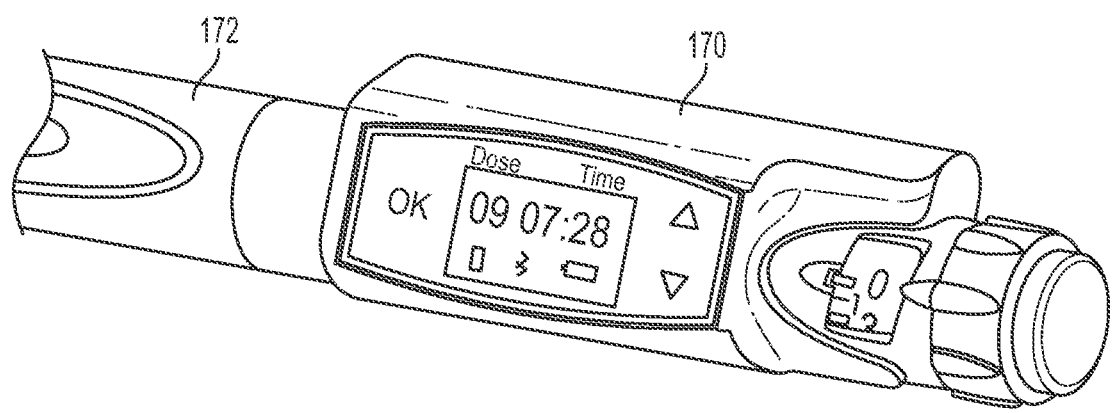
FIG. 4 is a perspective view of an exemplary embodiment of a smart pen accessory that is suitable for use with the medication delivery system shown in FIG. 1.

FIG. 4 is a perspective view of an exemplary embodiment of a smart pen accessory 170 that is suitable for use with the medication delivery system 102 shown in FIG. 1. The smart pen accessory 170 is one example of a device that can be used as part of the discrete medication delivery system 103 of FIG. 1. In particular, the smart pen accessory 170 cooperates with a "non-smart" insulin pen that lacks the intelligence and functionality of a smart insulin pen (as described above). The smart pen accessory 170 can be realized as a pen cap, a clip-on apparatus, a sleeve, or the like. The smart pen accessory 170 is attached to an insulin pen 172 such that the smart pen accessory 170 can measure the amount of insulin delivered by the insulin pen 172. The insulin dosage data is stored by the smart pen accessory 170 along with corresponding date/time stamp information. In certain embodiments, the smart pen accessory 170 can receive, store, and process additional patient-related or therapy-related data, such as glucose data. Indeed, the smart pen accessory 170 may also support various features and functions described above in the context of the smart insulin pen 160. For example, the smart pen accessory 170 may be configured to receive insulin dosage recommendations or instructions and/or recommended dosing times (or a recommended dosing schedule). Moreover, the smart pen accessory 170 may be configured and controlled to support other features and interactive functions described in more detail below.

Figure 5:
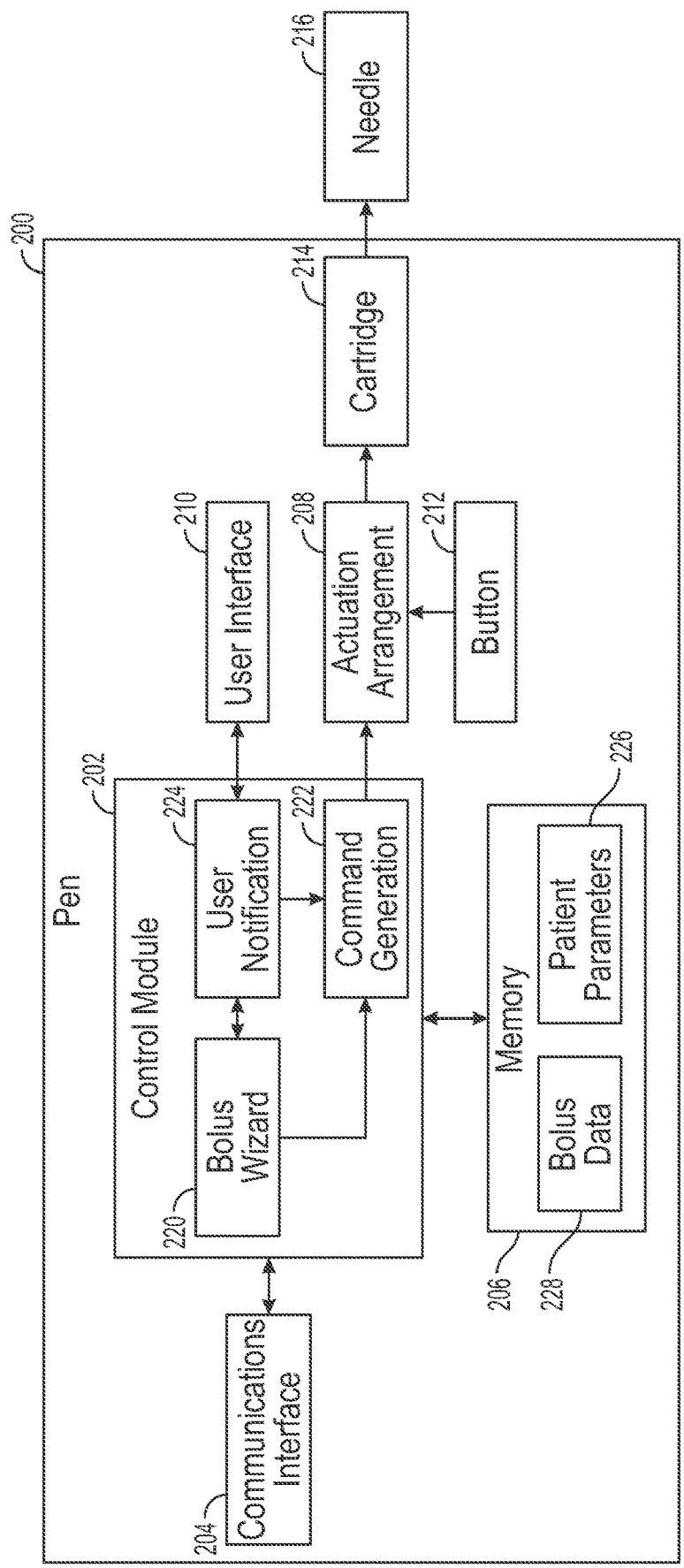
FIG. 5 is a block diagram of an exemplary embodiment of an injection pen suitable for use in the injection system of FIG. 1.

FIG. 5 depicts an exemplary embodiment of an injection pen 200 suitable for use as the discrete medication delivery system 103 of FIG. 1 in accordance with one or more embodiments. The injection pen 200 is one example of a device that can be used as part of the discrete medication delivery system 103 of FIG. 1. The illustrated injection pen 200 includes, without limitation, a pen controller 202, a communications interface 204, a data storage element (or memory) 206, an actuation arrangement 208, and user interface elements 210, 212. The pen controller 202 is coupled to the communications interface 204, the memory 206, the actuation arrangement 208, and the user interface elements 210, 212, and the pen controller 202 is suitably configured to support the operations, tasks, and/or processes described herein. In this regard, the pen controller 202 supports operation of the actuation arrangement 208 in response to manual actuation of a user interface element 212 to deliver a particular bolus amount of fluid from a fluid container 214 (e.g., a cartridge or reservoir) to an injection site in the body 104 of a patient via a needle 216.

The communications interface 204 generally represents the hardware, circuitry, logic, firmware and/or other components of the injection pen 200 that are coupled to the pen controller 202 and configured to support communications between the injection pen 200 and one or more external electronic devices of an injection system 100 (e.g., the blood glucose meter 106, the glucose sensing arrangement 108, and/or the electronic device 110). In exemplary embodiments, the communications interface 204 includes or is otherwise coupled to one or more transceivers capable of supporting wireless communications; however, in some embodiments, the communications interface 204 may be configured to support wired communications.

The user interface element(s) 210 generally represents the hardware, circuitry, logic, firmware and/or other components of the injection pen 200 configured to support user interactions between the pen controller 202 and a patient or user. The one or more user interface element(s) 210 associated with the injection pen 200 may include at least one input user interface element, such as, for example, a button, a keypad, a knob, a touch panel, a touchscreen, and/or the like. Additionally, the one or more user interface element(s) 210 may include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. In the illustrated embodiment, user interface element 212 represents an input user interface element of the injection pen 200 that is actuatable by a user to produce corresponding operation of the actuation arrangement 208 to deliver a bolus of fluid from the fluid container 214 via the needle 216. In one or more embodiments, the input user interface element 212 is realized as a tactile depressible button that is associated with the delivery of a bolus from the injection pen 200, and accordingly, the input user interface element 212 may alternatively be referred to herein, without limitation, as a delivery button.

The pen controller 202 generally represents the hardware, circuitry, logic, firmware and/or other component(s) of the injection pen 200 that is configured to determine bolus dosage commands for configuring or otherwise operating the actuation arrangement 208 to deliver fluid from the fluid container 214 and perform various additional tasks, operations, functions and/or operations described herein. Depending on the embodiment, the pen controller 202 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pen controller 202, or in any practical combination thereof.

In exemplary embodiments, the pen controller 202 includes or otherwise accesses the data storage element or memory 206, which may be realized using any sort of non-transitory computer-readable medium capable of storing programming instructions for execution by the pen controller 202. The computer-executable programming instructions, when read and executed by the pen controller 202, cause the pen controller 202 to perform the tasks, operations, functions, and processes described herein. In this regard, a control scheme or algorithm implemented by the pen controller 202 may be realized as control application code that is stored or otherwise maintained in the memory 206 and executed by the pen controller 202 to implement or otherwise provide one or more of the components in software. For example, the control application code may be executed by the controller 202 to generate a bolus wizard application 220 that calculates or otherwise determines the amount of fluid to be bolused to a patient. Similarly, the pen controller 202 may also implement or otherwise execute a command generation application 222 that converts a bolus amount from the bolus wizard application 220 into a corresponding command for operating or otherwise configuring the actuation arrangement 208 for dispensing the bolus amount from the container 214. The illustrated pen controller 202 also implements or otherwise executes a user notification application 224 that supports interactions with the patient or other users via the user interface element(s) 210 associated with the injection pen 200, as described in greater detail below.

Still referring to FIG. 5, the parameter registers 226 generally represent the hardware, circuitry and/or other components of the injection pen 200 that are configured to store the patient-specific physiological parameters or other control information utilized by the bolus wizard application 220 of the pen controller 202 in determining a bolus amount in a patient-specific manner. For example, the parameter registers 226 may store or otherwise maintain one or more patient-specific insulin sensitivity factor values, carbohydrate-to-insulin ratio values, insulin action speed values, target glucose values, and the like. The patient-specific insulin sensitivity factor value reflects the patient's sensitivity to insulin (e.g., an amount of drop in glucose level per unit of insulin administered). In practice, multiple different patient-specific insulin sensitivity factor values may be input by a user and stored by the injection pen 200 in association with particular time periods to support subdividing the day into multiple segments that reflect or otherwise account for diurnal variations in the patient's insulin sensitivity. The carbohydrate-to-insulin ratio value defines how many grams of carbohydrates one unit of insulin can compensate for, and similarly, multiple different carbohydrate-to-insulin ratio values may be input by a user and stored by the injection pen 200 in association with particular time periods to account for diurnal variations exhibited by the patient. The insulin action speed value represents the amount of time insulin remains active in the patient's body (e.g., the amount of time required to clear a unit of insulin).

In exemplary embodiments, the parameter registers 226 are capable of storing or otherwise maintaining a low target glucose value ($T_L$) and a high target glucose value ($T_H$), which are utilized when calculating the bolus amount. In this regard, the high target glucose value ($T_H$) is the desired glucose level that the user would like to achieve or stay below after delivering a bolus, and the low target glucose value ($T_L$) is the desired glucose level that the user would like to achieve or stay above after delivering a bolus. Again, multiple different sets of target glucose values may be input by a user and stored by the injection pen 200 in association with particular time periods to support subdividing the day into multiple segments.

In exemplary embodiments, the memory 206 also includes registers 228 (or other allocation) configured to store historical bolus data for the injection pen 200. In this regard, the bolus data portion 228 of memory 206 stores or otherwise maintains information identifying the respective amounts of previous boluses and the respective delivery times associated with those previous boluses. As described in greater detail below in the context of FIG. 3, the historical bolus data for the injection pen 200 is utilized to calculate, estimate, or otherwise determine the amount of active insulin on-board (IOB) in the body 104 of the patient using the patient-specific insulin action speed value.

In the embodiment of FIG. 5, the actuation arrangement 208 generally represents the hardware, circuitry and/or other electrical, mechanical, or electromechanical components of the injection pen 200 that are configured to enable or otherwise facilitate delivering boluses of fluid from the fluid container 214 to the patient's body 104 via the needle 216. For example, the actuation arrangement 208 may include a motor mechanically coupled to a drive train assembly configured to translate rotational motor motion into linear displacement of a slide, shaft, or the like that produces a corresponding displacement of a plunger or stopper within the fluid container 214 towards the needle 216. In an alternative embodiment, the actuation arrangement 208 includes adjustable or configurable drive train components that are configured to selectively restrict or otherwise limit the range of motion (or amount of displacement) of the plunger or stopper within the fluid container 214, and thereby limit the amount of fluid that may be dispensed from the injection pen 200 when an actuatable user interface element 212 of the injection pen 200 (e.g., a depressible delivery button) is manually manipulated.

It should be understood that FIG. 5 is a simplified representation of the injection pen 200 for purposes of explanation and is not intended to limit the subject matter described herein in any way. In this regard, although FIG. 5 depicts the user interface elements 210, 212 as being integrated with the injection pen 200, in various alternative embodiments, one or more of the user interface element 210, 212 may be integrated with another device in the injection system 100 that is communicatively coupled to the injection pen 200 (e.g., the electronic device 110). Furthermore, although FIG. 5 depicts the fluid container 214 being onboard the injection pen 200, it will be appreciated that the container 214 may be physically separate from the injection pen 200 and detachable, removable or otherwise replaceable upon depletion. Similarly, although FIG. 5 depicts the needle 216 as being separate from the injection pen 200 (e.g., a detachable or replaceable needle), in some embodiments, the needle 216 may be integrated or otherwise fixedly engaged with the housing of the injection pen 200. Additionally, while FIG. 5 depicts registers 226, 228 as being integrated with or into the memory 206, in various embodiments, either or both of the registers 226, 228 may be distinct or otherwise separate from memory 206, and the registers 226, 228 may be integrated with the pen controller 202 or with one another separate from the memory 206.

Referring again to FIG. 1, the analyte sensor 112 may communicate sensor data to the continuous medication delivery system 102 and/or the discrete medication delivery system 103 for use in regulating or controlling operation of the continuous medication delivery system 102 and/or the discrete medication delivery system 103. Alternatively or additionally, the analyte sensor 112 may communicate sensor data to one or more other components in the system 100, such as, without limitation: a user device 108 (for use with the patient care application 110); a data processing system 116; and/or a patient history and outcomes database 114.

The system 100 can support any number of user devices 108 linked to the particular user or patient. In this regard, a user device 108 may be, without limitation: a smartphone device; a laptop, desktop, or tablet computer device; a medical device; a wearable device; a global positioning system (GPS) receiver device; a system, component, or feature onboard a vehicle; a smartwatch device; a television system; a household appliance; a video game device; a media player device; or the like. For the example described here, the continuous medication delivery system 102 and/or the discrete medication delivery system 103 and the at least one user device 108 are owned by, operated by, or otherwise linked to a user/patient. Any given user device 108 can host, run, or otherwise execute the patient care application 110. In certain embodiments, for example, the user device 108 is implemented as a smartphone with the patient care application 110 installed thereon. In accordance with another example, the patient care application 110 is implemented in the form of a website or webpage, e.g., a website of a healthcare provider, a website of the manufacturer, supplier, or retailer of the continuous medication delivery system 102 and/or the discrete medication delivery system 103, or a website of the manufacturer, supplier, or retailer of the analyte sensor 112. In accordance with another example, the continuous medication delivery system 102 and/or the discrete medication delivery system 103 executes the patient care application 110 as a native function.

In certain embodiments, at least some of the features or output of the gesture-based event detection system 104 and/or the ancillary system(s) 106 can be used to influence features, functions, and/or therapy-related operations of the continuous medication delivery system 102 and/or the discrete medication delivery system 103. In particular, the systems 104, 106 may be suitably configured and operated to generate and provide output (e.g., data, control signals, markers, or flags) that indicates whether the user's behavior or activity is out of the ordinary, unusual, or has significantly changed relative to a currently implemented or active therapy behavior pattern of the user, such that the continuous medication delivery system 102 can dynamically respond in an appropriate manner that contemplates a change in user activity. Likewise, the systems 104, 106 may be suitably configured and operated to generate and provide output (e.g., data, control signals, markers, or flags) to the discrete medication delivery system 103 so that the user can take actions to adjust therapy As described in more detail below, the gesture-based event detection system 104 includes one or more sensors, detectors, measurement devices, and/or readers to automatically detect certain user gestures that correlate to user behavior, eating habits, work habits, or the like (e.g., work-related physical activity, commuting, eating at common meal times, sleeping, exercising, or watching television). The gesture-based event detection system 104 may communicate gesture data to the continuous medication delivery system 102 and/or the discrete medication delivery system 103, the user device 108, and/or the data processing system 116 for processing in an appropriate manner for use in regulating or controlling certain functions of the continuous medication delivery system 102 and/or the discrete medication delivery system 103. For example, the gesture data may be communicated to a user device 108, such that the user device 108 can process the gesture data and inform the user or the continuous medication delivery system 102 as needed (e.g., remotely regulate or control certain functions of the continuous medication delivery system 102). As another example, the gesture-based event detection system 104 may communicate the gesture data to one or more cloud computing systems or servers (such as a remote data processing system 116) for appropriate processing and handling in the manner described herein.

Similarly, an ancillary system 106 may include one or more sensors, detectors, measurement devices, and/or readers that obtain ancillary user status data that correlates to user activity, detectable behavior, eating habits, etc. In certain embodiments, an ancillary system 106 may include, cooperate with, or be realized as any of the following, without limitation: a heartrate monitor linked to the user; a blood pressure monitor linked to the user; a respiratory rate monitor linked to the user; a vital signs monitor linked to the user; a microphone; a thermometer (for the user's body temperature and/or the environmental temperature); a sweat detector linked to the user; an activity tracker linked to the user; a global positioning system (GPS); a clock, calendar, or appointment application linked to the user; a pedometer linked to the user; or the like. An ancillary system 106 may be configured and operated to communicate its output (user status data) to one or more components of the system 100 for analysis, processing, and handling in the manner described herein. In certain embodiments, user status data obtained from one or more ancillary systems 106 supplements the gesture data obtained from the gesture-based event detection system 104, such that user habits, physical behavior, and activity events are accurately and reliably detected.

In certain embodiments, the gesture-based event detection system 104, the continuous medication delivery system 102, and the discrete medication delivery system 103 are implemented as physically distinct and separate components, as depicted in FIG. 1. In such embodiments, the gesture-based event detection system 104 is external to the continuous medication delivery system 102 and/or the discrete medication delivery system 103 and is realized as an ancillary component, relative to the continuous medication delivery system 102 and/or the discrete medication delivery system 103. In accordance with alternative embodiments, however, the continuous medication delivery system 102 and/or the discrete medication delivery system 103 and the gesture-based event detection system 104 can be combined into a single hardware component or provided as a set of attached hardware devices. For example, the continuous medication delivery system 102 and/or the discrete medication delivery system 103 may include the gesture-based event detection system 104 or integrate the functionality of the system 104. Similarly, the analyte sensor 112 can be incorporated with the continuous medication delivery system 102, the discrete medication delivery system 103 or the gesture-based event detection system 104. These and other arrangements, deployments, and topologies of the system 100 are contemplated by this disclosure.

The at least one patient history and outcomes database 114 includes historical data related to the user's physical condition, physiological response to the medication regulated by the continuous medication delivery system 102 and/or the discrete medication delivery system 103, activity patterns or related information, eating patterns and habits, work habits, and the like. In accordance with embodiments where the continuous medication delivery system 102 and/or the discrete medication delivery system 103 is an insulin infusion device and the analyte sensor 112 is a glucose meter, sensor, or monitor, the database 114 can maintain any of the following, without limitation: historical glucose data and corresponding date/time stamp information; insulin delivery and dosage information; user-entered stress markers or indicators; gesture data (provided by the gesture-based event detection system 104) and corresponding date/time stamp information; ancillary user status data (provided by one or more ancillary systems 106) and corresponding date/time stamp data; diet or food intake history for the user; and any other information that may be generated by or used by the system 100 for purposes of controlling the operation of the continuous medication delivery system 102. In certain embodiments, the at least one patient history and outcomes database 114 can receive and maintain training data that is utilized to train, configure, and initialize the system 100 based on historical user behavior, physiological state, operation of the continuous medication delivery system 102 and/or the discrete medication delivery system 103, and user-identified activity events.

A patient history and outcomes database 114 may reside at a user device 108, at the continuous medication delivery system 102, at the discrete medication delivery system 103, at a data processing system 116, or at any network-accessible location (e.g., a cloud-based database or server system). In certain embodiments, a patient history and outcomes database 114 may be included with the patient care application 110. The patient history and outcomes database 114 enables the system 100 to generate recommendations, warnings, and guidance for the user and/or to regulate the manner in which the continuous medication delivery system 102 and/or the discrete medication delivery system 103 functions to administer therapy to the user, based on detected changes in the user's activity (which may be temporary, ongoing for an extended period of time, or somewhat permanent in nature).

Figure 6:
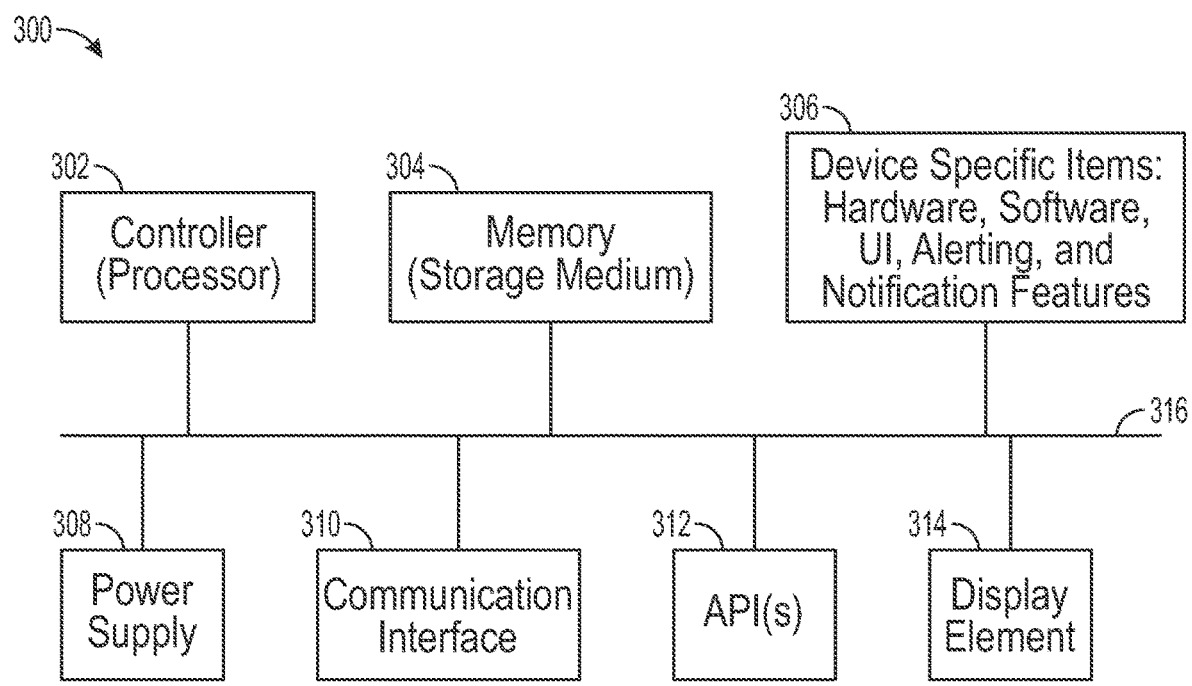
FIG. 6 is a block diagram representation of an exemplary embodiment of a computer-based or processor-based device suitable for deployment in the system shown in FIG. 1.

In accordance with certain embodiments, any or all of the components shown in FIG. 1 can be implemented as a computer-based or a processor-based device, system, or component having suitably configured hardware and software written to perform the functions and methods needed to support the features described herein. In this regard, FIG. 6 is a simplified block diagram representation of an exemplary embodiment of a computer-based or processor-based device 300 that is suitable for deployment in the system 100 shown in FIG. 1 (e.g., a user device).

The illustrated embodiment of the device 300 is intended to be a high-level and generic representation of one suitable platform. In this regard, any computer-based or processor-based component of the system 100 can utilize the architecture of the device 300. The illustrated embodiment of the device 300 generally includes, without limitation: at least one controller (or processor) 302; a suitable amount of memory 304 that is associated with the at least one controller 302; device-specific items 306 (including, without limitation: hardware, software, firmware, user interface (UI), alerting, and notification features); a power supply 308 such as a disposable or rechargeable battery; a communication interface 310; at least one application programming interface (API) 312; and a display element 314. Of course, an implementation of the device 300 may include additional elements, components, modules, and functionality configured to support various features that are unrelated to the primary subject matter described here. For example, the device 300 may include certain features and elements to support conventional functions that might be related to the particular implementation and deployment of the device 300. In practice, the elements of the device 300 may be coupled together via at least one bus or any suitable interconnection architecture 316.

The at least one controller 302 may be implemented or performed with a general purpose processor, a content addressable memory, a microcontroller unit, a digital signal processor, an application specific integrated circuit, a field programmable gate array, any suitable programmable logic device, discrete gate or transistor logic, discrete hardware components, or any combination designed to perform the functions described here. Moreover, the at least one controller 302 may be implemented as a combination of computing devices, e.g., a combination of a digital signal processor and a microprocessor, a plurality of microprocessors, one or more microprocessors in conjunction with a digital signal processor core, or any other such configuration.

The memory 304 may be realized as at least one memory element, device, module, or unit, such as: RAM memory, flash memory, EPROM memory, EEPROM memory, registers, a hard disk, a removable disk, a CD-ROM, or any other form of storage medium known in the art. In this regard, the memory 304 can be coupled to the at least one controller 302 such that the at least one controller 302 can read information from, and write information to, the memory 304. In the alternative, the memory 304 may be integral to the at least one controller 302. As an example, the at least one controller 302 and the memory 304 may reside in an ASIC. At least a portion of the memory 304 can be realized as a computer storage medium that is operatively associated with the at least one controller 302, e.g., a tangible, non-transitory computer-readable medium having computer-executable instructions stored thereon. The computer-executable instructions are configurable to be executed by the at least one controller 302 to cause the at least one controller 302 to perform certain tasks, operations, functions, and processes that are specific to the particular embodiment. In this regard, the memory 304 may represent one suitable implementation of such computer-readable media. Alternatively or additionally, the device 300 could receive and cooperate with computer-readable media (not separately shown) that is realized as a portable or mobile component or platform, e.g., a portable hard drive, a USB flash drive, an optical disc, or the like.

The device-specific items 306 may vary from one embodiment of the device 300 to another. For example, the device-specific items 306 will support: sensor device operations when the device 300 is realized as a sensor device; smartphone features and functionality when the device 300 is realized as a smartphone; activity tracker features and functionality when the device 300 is realized as an activity tracker; smart watch features and functionality when the device 300 is realized as a smart watch; medical device features and functionality when the device is realized as a medical device; etc. In practice, certain portions or aspects of the device-specific items 306 may be implemented in one or more of the other blocks depicted in FIG. 6.

If present, the UI of the device 300 may include or cooperate with various features to allow a user to interact with the device 300. Accordingly, the UI may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 300. The UI may include one or more graphical user interface (GUI) control elements that enable a user to manipulate or otherwise interact with an application via the display element 314. The display element 314 and/or the device-specific items 306 may be utilized to generate, present, render, output, and/or annunciate alerts, alarms, messages, or notifications that are associated with operation of the medication delivery system 102, associated with a status or condition of the user, associated with operation, status, or condition of the system 100, etc.

The communication interface 310 facilitates data communication between the device 300 and other components as needed during the operation of the device 300. In the context of this description, the communication interface 310 can be employed to transmit or stream device-related control data, patient-related user status (e.g., gesture data or status data), device-related status or operational data, sensor data, calibration data, and the like. It should be appreciated that the particular configuration and functionality of the communication interface 310 can vary depending on the hardware platform and specific implementation of the device 300. In practice, an embodiment of the device 300 may support wireless data communication and/or wired data communication, using various data communication protocols. For example, the communication interface 310 could support one or more wireless data communication protocols, techniques, or methodologies, including, without limitation: RF; IrDA (infrared); Bluetooth; BLE; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication interface 310 could support one or more wired/cabled data communication protocols, including, without limitation: Ethernet; powerline; home network communication protocols; USB; IEEE 1394 (Firewire); hospital network communication protocols; and proprietary data communication protocols.

The at least one API 312 supports communication and interactions between software applications and logical components that are associated with operation of the device 300. For example, one or more APIs 312 may be configured to facilitate compatible communication and cooperation with the patient care application 110, and to facilitate receipt and processing of data from sources external to the device 300 (e.g., databases or remote devices and systems).

The display element 314 is suitably configured to enable the device 300 to render and display various screens, recommendation messages, alerts, alarms, notifications, GUIs, GUI control elements, drop down menus, auto-fill fields, text entry fields, message fields, or the like. Of course, the display element 314 may also be utilized for the display of other information during the operation of the device 300, as is well understood. Notably, the specific configuration, operating characteristics, size, resolution, and functionality of the display element 314 can vary depending upon the implementation of the device 300.

Figure 7:
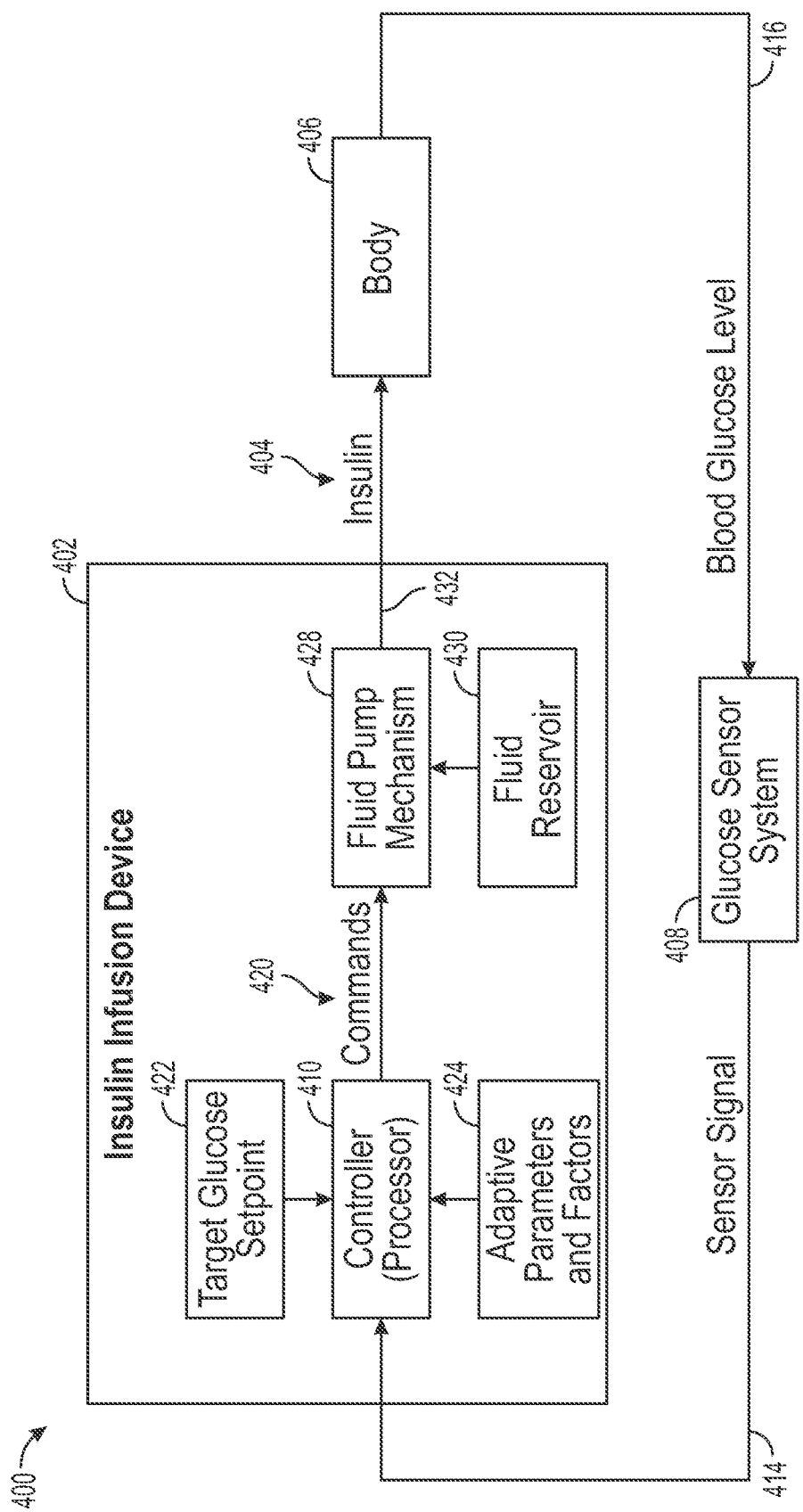
FIG. 7 is a block diagram representation of a closed loop glucose control system arranged in accordance with certain embodiments.

As mentioned above, the medication delivery system 102 is suitably configured and programmed to support an automatic mode to automatically control delivery of insulin to the user. In this regard, FIG. 7 is a simplified block diagram representation of a closed loop glucose control system 400 arranged in accordance with certain embodiments. The system 400 is one example of a system that can be used as part of the continuous medication delivery system 102 of FIG. 1. The system 400 depicted in FIG. 7 functions to regulate the rate of fluid infusion into a body of a user based on feedback from an analyte concentration measurement taken from the body. In particular embodiments, the system 400 is implemented as an automated control system for regulating the rate of insulin infusion into the body of a user based on a glucose concentration measurement taken from the body. The system 400 is designed to model the physiological response of the user to control an insulin infusion device 402 in an appropriate manner to release insulin 404 into the body 406 of the user in a similar concentration profile as would be created by fully functioning human B-cells when responding to changes in blood glucose concentrations in the body. Thus, the system 400 simulates the body's natural insulin response to blood glucose levels and not only makes efficient use of insulin, but also accounts for other bodily functions as well since insulin has both metabolic and mitogenic effects.

Certain embodiments of the system 400 include, without limitation: the insulin infusion device 402; a glucose sensor system 408 (e.g., the analyte sensor 112 shown in FIG. 1); and at least one controller 410, which may be incorporated in the insulin infusion device 402 as shown in FIG. 7. The glucose sensor system 408 generates a sensor signal 414 representative of blood glucose levels 416 in the body 406, and provides the sensor signal 414 to the at least one controller 410. The at least one controller 410 receives the sensor signal 414 and generates commands 420 that regulate the timing and dosage of insulin 404 delivered by the insulin infusion device 402. The commands 420 are generated in response to various factors, variables, settings, and control algorithms utilized by the insulin infusion device 402. For example, the commands 420 (and, therefore, the delivery of insulin 404) can be influenced by a target glucose setpoint value 422 that is maintained and regulated by the insulin infusion device 402. Moreover, the commands 420 (and, therefore, the delivery of insulin 404) can be influenced by any number of adaptive parameters and factors 424. The adaptive parameters and factors 424 may be associated with or used by: a therapy control algorithm of the insulin infusion device 402; a digital twin model of the patient, which can be used to recommend insulin dosages; a meal prediction algorithm; a user glucose prediction algorithm; or the like.

Generally, the glucose sensor system 408 includes a continuous glucose sensor, sensor electrical components to provide power to the sensor and generate the sensor signal 414, a sensor communication system to carry the sensor signal 414 to the at least one controller 410, and a sensor system housing for the electrical components and the sensor communication system. As mentioned above with reference to FIG. 6, the glucose sensor system 408 may be implemented as a computer-based or processor-based component having the described configuration and features.

Typically, the at least one controller 410 includes controller electrical components and software to generate commands for the insulin infusion device 402 based on the sensor signal 414, the target glucose setpoint value 422, the adaptive parameters and factors 424, and other user-specific parameters, settings, and factors. The at least one controller 410 may include a controller communication system to receive the sensor signal 414 and issue the commands 420.

Generally, the insulin infusion device 402 includes a fluid pump mechanism 428, a fluid reservoir 430 for the medication (e.g., insulin), and an infusion tube to infuse the insulin 404 into the body 406. In certain embodiments, the insulin infusion device 402 includes an infusion communication system to handle the commands 420 from the at least one controller 410, electrical components and programmed logic to activate the fluid pump mechanism 428 motor according to the commands 420, and a housing to hold the components of the insulin infusion device 402. Accordingly, the fluid pump mechanism 428 receives the commands 420 and delivers the insulin 404 from the fluid reservoir 430 to the body 406 in accordance with the commands 420. It should be appreciated that an embodiment of the insulin infusion device 402 can include additional elements, components, and features that may provide conventional functionality that need not be described herein. Moreover, an embodiment of the insulin infusion device 402 can include alternative elements, components, and features if so desired, as long as the intended and described functionality remains in place. In this regard, as mentioned above with reference to FIG. 6, the insulin infusion device 402 may be implemented as a computer-based or processor-based components having the described configuration and features, including the display element 214 or other device-specific items 206 as described above.

The at least one controller 410 is configured and programmed to regulate the operation of the fluid pump mechanism 428 and other functions of the insulin infusion device 402. The at least one controller 410 controls the fluid pump mechanism 428 to deliver the fluid medication (e.g., insulin) from the fluid reservoir 430 to the body 406. As mentioned above, the at least one controller 410 can be housed in the infusion device housing, wherein the infusion communication system is an electrical trace or a wire that carries the commands 420 from the at least one controller 410 to the fluid pump mechanism 428. In alternative embodiments, the at least one controller 410 can be housed in the sensor system housing, wherein the sensor communication system is an electrical trace or a wire that carries the sensor signal 414 from the sensor electrical components to the at least one controller 410. In accordance with some embodiments, the at least one controller 410 has its own housing or is included in a supplemental or ancillary device. In other embodiments, the at least one controller 410, the insulin infusion device 402, and the glucose sensor system 408 are all located within one common housing.

Referring again to FIG. 1, the gesture-based event detection system 104 employs at least one sensor to obtain corresponding user-specific sensor data. The obtained user-specific sensor data is processed or analyzed by the gesture-based event detection system 104 and/or by another suitably configured device or component of the system 100 to determine whether the user's current behavior reflects a significant or measurable change in activity, relative to a currently implemented, active, or monitored therapy behavior pattern of the user. The obtained user-specific sensor data may also be processed or analyzed to obtain certain activity-related parameters, characteristics, and/or metadata for the user. For example, the obtained user-specific sensor data may identify, include, or indicate any or all of the following, without limitation: timestamp data corresponding to the occurrence of detected events; a type, category, or classification of the detected physical behavior or activity; location data; user posture or position information; etc.

The gesture-based event detection system 104 may include, cooperate with, or be realized as a motion-based physical behavior detection system, an activity-based physical behavior detection system, an image or video-based activity detection system, or the like. In certain embodiments, the system 104 may be realized as a unitary "self-contained" wearable system that communicates with one or more other components of the system 100. For example, the system 104 can be implemented with at least one wearable device such as an activity monitor device, a smart watch device, a smart bracelet or wristband device, or the like. In some embodiments, the system 104 may be realized as at least one portable or wearable device that includes or communicates with one or more external or ancillary sensor devices, units, or components. For example, the system 104 can be implemented with a wearable or portable smart device that is linked with one or more external sensors worn or carried by the user. These and other possible deployments of the system 104 are contemplated by this disclosure. In this regard, United States patent publication number US 2020/0135320 and United States patent publication number US 2020/0289373 disclose gesture-based event detection systems that are suitable for use as the system 104; the entire content of these United States patent documents is incorporated by reference herein.

Figure 8:
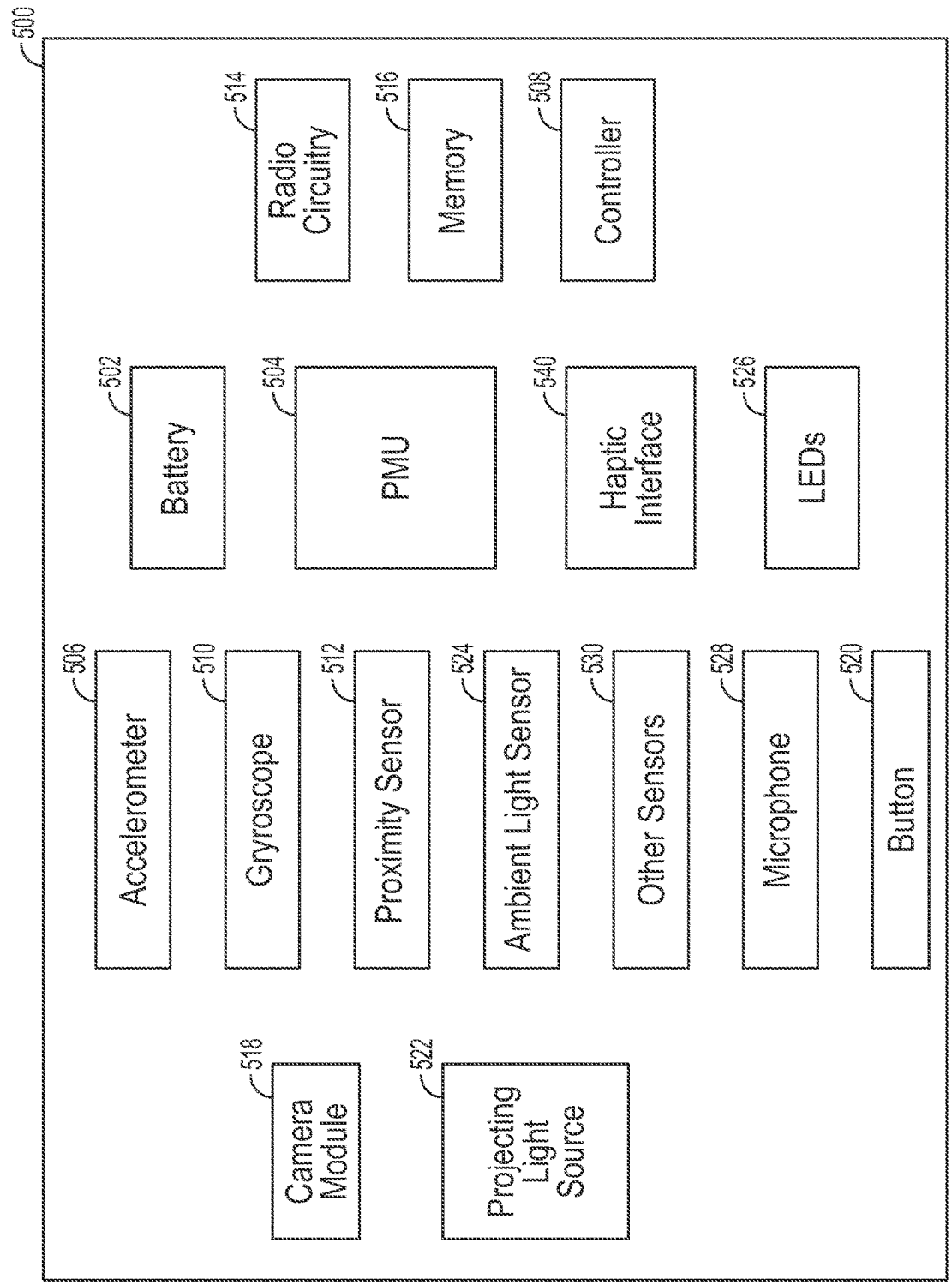
FIG. 8 is a block diagram representation of a gesture-based event detection system arranged in accordance with certain embodiments.

FIG. 8 is a block diagram representation of a gesture-based event detection system 500 arranged in accordance with certain embodiments. The system 500 is suitable for use with the system 100 shown FIG. 1. Some or all components of the gesture-based event detection system 500 can be used to implement the gesture-based event detection system 104 of FIG. 1. In certain embodiments, the system 500 is deployed as a wearable electronic device in the form factor of a bracelet or wristband that is worn around the wrist or arm of a user's dominant hand. The system 500 may optionally be implemented using a modular design, wherein individual modules include one or more subsets of the disclosed components and overall functionality. The user may choose to add specific modules based on personal preferences and requirements.

The system 500 includes a battery 502 and a power management unit (PMU) 504 to deliver power at the proper supply voltage levels to all electronic circuits and components. The PMU 504 may also include battery-recharging circuitry. The PMU 504 may also include hardware, such as switches, that allows power to specific electronics circuits and components to be cut off when not in use.

When there is no movement-based or gesture-based behavior event in progress, most circuitry and components in the system 500 are switched off to conserve power. Only circuitry and components that are required to detect or help predict the start of a behavior event of interest may remain enabled. For example, if no motion is being detected, all sensor circuits but an accelerometer 506 may be switched off and the accelerometer 506 may be put in a low-power wake-on-motion mode or in another lower power mode that consumes less power and uses less processing resources than its high performance active mode. A controller 508 of the system 500 may also be placed into a low-power mode to conserve power. When motion or a certain motion pattern is detected, the accelerometer 506 and/or the controller 508 may switch into a higher power mode and additional sensors such as, for example, a gyroscope 510 and/or a proximity sensor 512 may also be enabled. When a potential start of a movement-based or gesture-based event is detected, memory variables for storing event-specific parameters, such as gesture types, gesture duration, etc. can be initialized.

In another example, upon detection of user motion, the accelerometer 506 switches into a higher power mode, but other sensors remain switched off until the data from the accelerometer 506 indicates that the start of a behavior event has likely occurred. At that point in time, additional sensors such as the gyroscope 510 and the proximity sensor 512 may be enabled.

In another example, when there is no behavior event in progress, both the accelerometer 506 and gyroscope 510 are enabled but at least one of either the accelerometer 506 or the gyroscope 510 is placed in a lower power mode compared to their regular power mode. For example, the sampling rate may be reduced to conserve power. Similarly, the circuitry required to transfer data from the system 500 to a destination device may be placed in a lower power mode. For example, radio circuitry 514 could be disabled. Similarly, the circuitry required to transfer data from the system 500 may be placed in a lower power mode. For example, the radio circuitry 514 could be disabled until a possible or likely start of a behavior event has been determined. Alternatively, it may remain enabled but in a low power state to maintain the connection between the system 500 and one or more other components of the system 100, but without transferring user status data, sensor data, or the like.

In yet another example, all motion-detection related circuitry may be switched off if, based on certain metadata, it is determined that the occurrence of a particular behavior event, such as a food intake event, is unlikely. This may be desirable to further conserve power. Metadata used to make this determination may, among other things, include one or more of the following: time of the day, location, ambient light levels, proximity sensing, and detection that the system 500 has been removed from the wrist or hand, detection that the system 500 is being charged, or the like. Metadata may be generated and collected by the system 500. Alternatively, metadata may be collected by another device that is external to the system 500 and is configured to directly or indirectly exchange information with the system 500. It is also possible that some metadata is generated and collected by the system 500, while other metadata is generated and collected by a device that is external to the system 500. In case some or all of the metadata is generated and collected external to the system 500, the system 500 may periodically or from time to time power up its radio circuitry 514 to retrieve metadata related information from another device.

In certain embodiments, some or all of the sensors may be turned on or placed in a higher power mode if certain metadata indicates that the occurrence of a particular behavior event, such as the user beginning to work, jog, or eat, is likely. Metadata used to make this determination may, among other things, include one or more of the following: time of the day; location; ambient light levels; proximity sensing; historical user behavior patterns. Some or all of the metadata may be collected by the system 500 or by an ancillary device that cooperates or communicates with the system 500, as mentioned above.

User status data used to track certain aspects of a user's behavior may be stored locally inside memory 516 of the system 500 and processed locally using the controller 508 of the system 500. User status data may also be transferred to the medication delivery system 102, the patient care application 110, and/or one or more of the database 114 mentioned above with reference to FIG. 1 (such that the user status data can be processed, analyzed, or otherwise utilized by the applications or components that receive the user status data). It is also possible that some of the processing and analysis are performed locally by the system 500, while further processing and analysis are performed by one or more other components of the system 100.

The detection of the start of a behavior event, such as the start of a work activity, may trigger the power up and/or activation of additional sensors and circuitry, such as a camera 518. Power up and/or activation of additional sensors and circuitry may occur at the same time as the detection of the behavior event of interest or some time thereafter. Specific sensors and circuitry may be turned on only at specific times during a detected event, and may be switched off otherwise to conserve power. It is also possible that the camera 518 only gets powered up or activated upon explicit user intervention such as, for example, pushing and holding a button 520. Releasing the button 520 may turn off the camera 518 to conserve power.

When the camera 518 is powered up, a projecting light source 522 may also be enabled to provide visual feedback to the user about the area that is within view of the camera or to otherwise illuminate the field of view. Alternatively, the projecting light source 522 may only be activated sometime after the camera 518 has been activated. In certain cases, additional conditions may need to be met before the projecting light source 522 is activated. Such conditions may include: the determination that the projecting light source 522 is likely aiming in the direction of the object of interest; the determination that the system 500 is not moving excessively; or the like. In some embodiments, one or more light emitting diodes (LEDs) 526 may be used as the projecting light source 522.

Images may be tagged with additional information or metadata such as: camera focal information; proximity information from the proximity sensor 512; ambient light levels information from an ambient light sensor 524; timestamp information; etc. Such additional information or metadata may be used during the processing and analysis of the user status data.

The projecting light source 522 may also be used to communicate other information. As an example, an ancillary device may use inputs from one or more proximity sensors 512, process those inputs to determine if the camera 518 is within the proper distance range from the object of interest, and use one or more light sources to communicate that the camera is within the proper distance range, that the user needs to increase the distance between camera and the object of interest, or that the user needs to reduce the distance between the camera and the object of interest.

The projecting light source 522 may also be used in combination with the ambient light sensor 524 to communicate to the user if the ambient light is insufficient or too strong for an adequate quality image capture. The projecting light source 522 may also be used to communicate information including, but not limited to, a low battery situation or a functional defect.

The projecting light source 522 may also be used to communicate dietary coaching information. As an example, the projecting light source 522 might, among other things, indicate if not enough or too much time has expired since a previous food intake event, or may communicate to the user how he/she is doing against specific dietary goals.

Signaling mechanisms to convey specific messages using one or more projecting light sources 522 may include, but are not limited to, one or more of the following: specific light intensities or light intensity patterns; specific light colors or light color patterns; specific spatial or temporal light patterns. Multiple mechanisms may also be combined to signal one specific message.

A microphone 528 may be used by the user to add specific or custom labels or messages to a detected event and/or image. In certain embodiments, audio captured by the microphone 528 can be processed to assist in the determination of whether the user is eating, drinking, commuting, exercising, working, or resting. Audio snippets may be processed by a voice recognition engine.

In certain embodiments, the accelerometer 506 (possibly combined with other sensors, including other inertial sensors) may, in addition to tracking at least one parameter that is directly related to a gesture-based behavior event, also be used to track one or more parameters that are not directly related to that particular event. Such parameters may, among other things, include physical activity, sleep, stress, or illness.

In addition to the particular sensors, detectors, and components mentioned above, the system 500 may include or cooperate with any number of other sensors 530 as appropriate for the particular embodiment. For example, and without limitation, the system 500 may include or cooperate with any or all of the following: a heartrate monitor; a physiological characteristic or analyte sensor; a continuous glucose monitor; a GPS receiver; and any other sensor, monitor, or detector mentioned elsewhere herein. The system 500 obtains user status data from one or more of its sensors, detectors, and sources, wherein the user status data indicates a stressful activity of the user. The user status data can be analyzed and processed by the system 500 (and/or by one or more other components of the system 100) to determine whether the user's current behavior is consistent with normally expected behavior or activity. In certain embodiments, the system 500 and/or an ancillary system 106 or device determines the user's activity and related behavior primarily based on the output of user-worn motion sensors, movement sensors, one or more inertial sensors (e.g., one or more accelerometers and/or one or more gyroscopes), one or more GPS sensors, one or more magnetometers, one or more force or physical pressure sensors, or the like, which are suitably configured, positioned, and arranged to measure physical movement or motion of the user's limbs, digits, joints, facial features, head, and/or other body parts.

In some embodiments, the system 500 includes at least one haptic interface 540 that is suitably configured and operated to provide haptic feedback as an output. The at least one haptic interface 540 generates output(s) that can be experienced by the sense of touch by the user, e.g., mechanical force, vibration, movement, temperature changes, or the like. Haptic feedback generated by the at least one haptic interface 540 may represent or be associated with one or more of the following, without limitation: reminders; alerts; confirmations; notifications; messages; numerical values (such as measurements); status indicators; or any other type of output provided by the system 500.

In certain embodiments, the user status data (e.g., sensor data) is provided to a gesture recognizer unit or processor. To this end, sensor data may be sent in raw format. Alternatively, a source of sensor data may perform some processing (e.g., filtering, compression, or formatting) on raw sensor data before sending the processed sensor data to the gesture recognizer unit. The gesture recognizer unit analyzes the incoming sensor data and converts the incoming sensor data into a stream of corresponding gestures, which may be predetermined or otherwise classified or categorized. The gesture recognizer unit may use one or more ancillary inputs (such as the output from one or more ancillary systems 106) to aid in the gesture determination process. Nonlimiting examples of an ancillary input include: time of day; the probability of a specific gesture occurring based on statistical analysis of historical gesture data for that user; geographical location; heart rate; other physiological sensor inputs. Other ancillary inputs are also possible.

The output of the gesture recognizer unit—the detected gestures—can be sent to an event detector or processor. The event detector analyzes the incoming stream of gestures to determine if the start of an event of interest (e.g., eating a meal, going to bed, working out) has occurred, whether an event is ongoing, whether an event has ended, or the like. Although this description mentions meal detection, the gesture-based event detection system 500 may be suitably configured to monitor other types of physical behavior or activities. Such activities include, without limitation: reading; sleeping; smoking; getting dressed; driving; walking; commuting; working; exercising; turning down a bed; making a bed; brushing teeth; combing hair; talking on the phone; inhaling or injecting a medication; and activities related to hand hygiene or personal hygiene.

Referring again to FIG. 1, the output of the gesture-based event detection system 104 (in some embodiments, supplemented with the output of the ancillary system(s) 106) can be used to detect significant or relevant changes in the patient's activity or usual routine. For example, gesture detection can be leveraged to identify any or all of the following events, without limitation: a change in eating habits or eating patterns; eating, working, sleeping, or exercising at unusual times; eating, working, sleeping, or exercising for periods of time that are longer or shorter than usual; consuming unusual types of food or drink; eating at restaurants that are out of the ordinary. Detected changes in the user's activity can inform certain functions, features, and/or therapy-related operations of the system 100. For example, detected changes in patient activity can influence one or more parameters of a closed loop medication delivery algorithm employed by the medication delivery system 102. Thus, a "nominal" or "default" therapy control algorithm may be active or implemented when the user's activity tracks a typical or routine pattern of behavior, and a different, altered, modified, or updated therapy control algorithm may be temporarily activated or utilized when the currently detected user activity changes. Any number of different types, classifications, categories, or levels of therapy control algorithms can be supported by the system described herein, as needed to contemplate detectable (and distinguishable) user activity patterns.

As another example, detected changes in activity can trigger modified adjustment of a digital twin model of the patient that simulates the patient's physiological response to medication. In this regard, an adaptive training or learning scheme can be used to dynamically train the digital twin model in an ongoing manner. However, in response to detected changes in the user's activity, a different, modified, or altered adaptive training scheme can be used to dynamically train the digital twin model in a manner that is appropriate for the currently detected behavior pattern. Any number of different types, classifications, categories, or levels of adaptive training schemes can be supported by the system described herein, as needed to contemplate detectable (and distinguishable) user activity patterns.

As another example, detected changes in activity can trigger adjustment of a currently active meal prediction algorithm, a currently active glucose prediction algorithm (when the analyte sensor 112 is realized as a glucose sensor), and/or a currently active dosage calculation algorithm. Similarly, detected changes in activity can trigger the selection, activation, or enablement of a different meal prediction algorithm, a different glucose prediction algorithm (when the analyte sensor 112 is realized as a glucose sensor), and/or a different dosage calculation algorithm. Any number of different types, classifications, categories, or levels of these therapy-related algorithms can be supported by the system described herein, as needed to contemplate detectable (and distinguishable) user activity patterns.

As yet another example, detected changes in user activity may reset, pause, alter, or restart an adaptive training scheme or an adaptive learning period during which at least one feature, function, setting, or model associated with the medication delivery system is adaptively trained or adjusted. In accordance with certain embodiments, operation of the medication delivery device 102 can be controlled or regulated based on a determination that the user's normal or routine activity has changed by some measurable amount. For example, if the system 100 determines (from an analysis of user gesture data) that the user's regular work, sleep, and/or eating schedule has changed, then certain adaptive, training, or learning functions of the medication delivery device 102 can be temporarily halted or frozen under the assumption that something unusual has occurred in the user's normally predictable daily routine. Accordingly, information and data that would normally be collected and used for adaptive training/learning need not be considered during periods of detected unusual or different user behavior.

Figure 9:
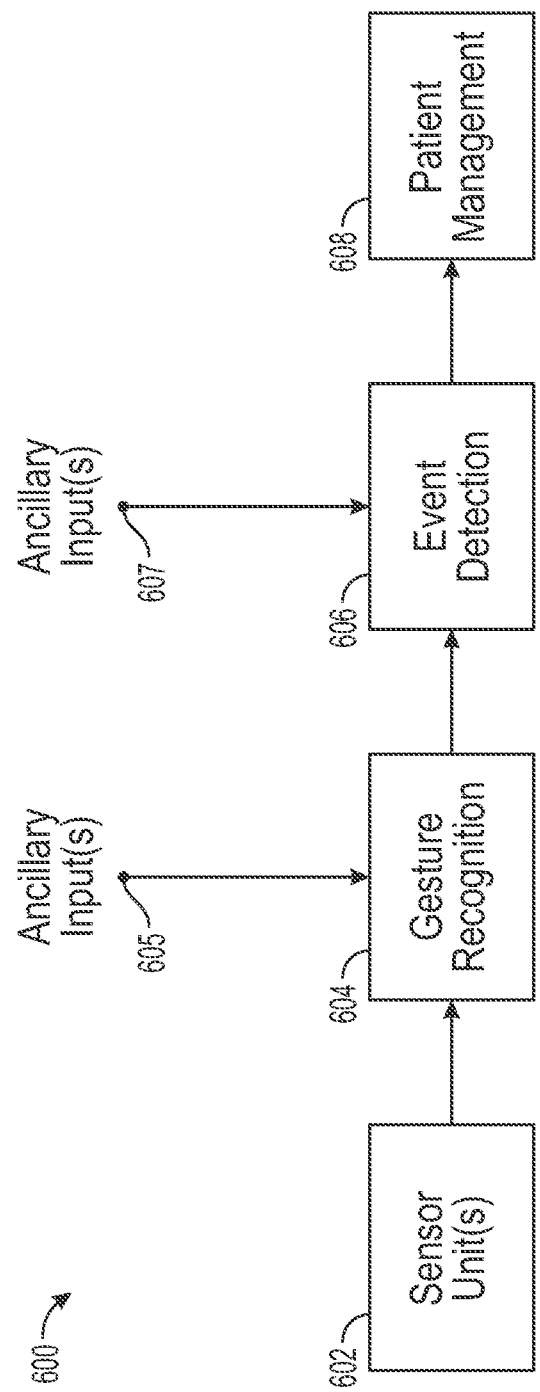
FIG. 9 is a block diagram representation of an embodiment of a gesture-informed patient management system in accordance with certain embodiments.

FIG. 9 is a simplified block diagram representation of an embodiment of a gesture-informed patient management system 600. The depicted patient management system 60 includes, without limitation, one or more sensor units 602, a gesture recognition unit 604, an event detection unit 606, and a patient management unit 608. Some or all components of the gesture-informed patient management system 600 can be used to implement the gesture-based event detection system 104 of FIG. 1.

The sensor unit(s) 602 generally represent the sensor(s) embedded in, integrated with, or otherwise associated with one or more portable or wearable devices associated with a patient, such as, for example, an activity tracker, a smart watch, a wristband, a ring, a mobile phone, or a portable electronic medical device (e.g., a continuous glucose monitoring device, an infusion device, an injection pen, and/or the like). For example, in one or more exemplary embodiments, the sensor unit(s) 602 include an accelerometer (e.g., accelerometer 506) and a gyroscope (e.g., gyroscope 510) associated with a smart watch. That said, it should be appreciated the patient management system 600 is not limited to any particular type, configuration, or number of sensor unit(s) 602, and in practice, the sensor unit(s) 602 may include one or more of the following sensing arrangements: accelerometers, gyroscopes, magnetometers, image sensors, cameras, optical sensors, proximity sensors, pressure sensors, odor sensors, gas sensors, Global Positioning Systems (GPS) receivers, microphones, galvanic skin response sensors, thermometers, ambient light sensors, UV sensors, electrodes for electromyographic ("EMG") potential detection, bio-impedance sensors, spectrometers, glucose sensors, heart rate sensors, pulse sensors, touchscreen or capacitive sensors. In this regard, the output of the sensor unit(s) 602 may include any sort of motion data, location data, physiological data (e.g., temperature, heart rate, pulse, galvanic skin response, blood or body chemistry, and/or the like), or other sensor data depending on the sensor type. The output of the sensor unit(s) 602 may be communicated to the gesture recognition unit 604 wirelessly or via wires, in analog or digital form, directly or indirectly (e.g., intermediated by gating and/or clocking circuits, analog-to-digital converters, and/or the like).

The gesture recognition unit 604 generally represents a software application or component of the patient management system 600 that receives the sensor data signals from the sensor unit(s) 602 and analyzes the received sensor data to detect or otherwise identify gestures performed by the patient based on the received sensor data. In this regard, a gesture generally represents a discrete set of one or more physical movements having associated spatial and/or temporal characteristics that are distinguishable from other gestures. For example, as described in United States Patent Publication Number 2020/0289373, the gesture recognition unit 604 may utilize machine learning or other artificial techniques to map different subsets of sensor data within a stream of received sensor data to different gesture features, which, in turn, are then analyzed to classify or otherwise resolve the different subsets of the sensor data and corresponding gesture features into a particular combination or sequence of gestures performed by the patient. In one or more embodiments, the gesture recognition unit 604 fuses or otherwise combines concurrent or otherwise temporally-associated accelerometer data and gyroscope data to obtain an orientation vector, with the concurrent or temporally-associated combinations of accelerometer data, gyroscope data, and fused orientation vectors being input to a feature generator, which, in turn, generates a corresponding stream of gesture features, which, in turn are input to the gesture recognition model which classifies or otherwise resolves the stream of gesture features into corresponding gestures. In exemplary embodiments, the gesture recognition unit 604 also associates or otherwise assigns a confidence metric to each gesture based on the gesture features. In this regard, for a given stream of sensor data received by the gesture recognition unit 604, the gesture recognition unit 604 outputs a corresponding stream of gestures and associated confidence levels.

In some embodiments, the gesture recognition unit 604 receives one or more ancillary inputs 605 which may influence the gesture detection or the confidence or probability assigned to detected gestures. For example, the ancillary input 605 may include operational contextual data, such as, the current time of day, the current day of the week, the current month of the year, the current location of the patient, and/or the like, along with other patient-specific data such as historical gesture data associated with the patient, a patient profile associated with the patient or other patient-specific personalization that may be utilized by the gesture recognition unit 604 to influence manner in which particular gesture features are mapped to a gesture for the particular patient. In this regard, statistical analysis of the historical gesture data and potentially other patient-specific data may be utilized to determine or otherwise assign probabilities of a specific gesture occurring based on the current operational context. It should be noted that there are any number of different types of ancillary input data that may be correlative to the occurrence or non-occurrence of a particular gesture, and the subject matter described herein is not limited to any particular type or combination of ancillary inputs 605 that may be utilized by the gesture recognition unit 604.

In one or more embodiments, the executable code or programming instructions corresponding to the gesture recognition unit 604 is stored or otherwise maintained in a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by a processor or other processing system. For example, in one or more exemplary embodiments, the computer-executable programming instructions corresponding to the gesture recognition unit 604 are stored in a data storage element (e.g., memory 416) of a wearable electronic device including the sensor unit(s) 602, and, when read and executed by a processing system (e.g., controller 408) of the wearable electronic device, the instructions cause the wearable electronic device to generate the gesture recognition unit 604 at the wearable electronic device. In this regard, in some embodiments, the wearable electronic device may transmit or otherwise provide signals or data indicating a stream of detected gestures and associated confidence levels to another device for further processing and/or analysis. That said, in other embodiments, the gesture recognition unit 604 may be implemented at or on a patient's mobile phone or other portable electronic device (e.g., user device 108) that receives sensor data signals from the sensor unit(s) 602 via a wireless network, or be implemented at or on a cloud computing system or remote server that receives the sensor data signals from the sensor unit(s) 602 via the Internet, a cellular network, or the like.

Still referring to FIG. 9, the event detection unit 606 generally represents a software application or component of the patient management system 600 that receives the detected gestures and confidence levels from the from the gesture recognition unit 604 and analyzes the received gesture data to detect or otherwise identify events or activities performed by the patient based on the received gesture data. For example, as described in United States Patent Publication Number 2020/0289373, the event detection unit 606 may utilize machine learning or other artificial techniques to map a stream of detected gestures and associated confidence levels into a particular event or activity being performed by the patient based on the type of gestures detected, the sequence of detected gestures, the temporal relationship between gestures and/or the confidence metrics assigned to the detected gestures. In this manner, the event detection unit 606 may map lower-level gestures into a higher-level physical behavior while filtering or otherwise deemphasizing false positives or spurious gestures. Thus, for a given stream of detected gestures received by the event detection unit 606, the event detection unit 606 outputs an indication of a detected event or activity by the patient and an associated confidence or probability metric for the event. For example, for a sequence of detected food intake gestures may be mapped or otherwise recognized as a food intake event having a particular start time, pace, duration, and/or the like with an assigned level of confidence or probability influenced by the confidence associated with the detected food intake gestures and potentially other factors.

In a similar manner as described above for the gesture recognition unit 604, the event detection unit 606 may receive ancillary input 607 which may influence the event detection or the confidence or probability assigned to detected events. For example, the ancillary input 607 may include event log data associated with the patient that maintain data pertaining to historical events or activities by the patient (e.g., meals, exercise, sleep, boluses, glucose excursion events, and/or the like), with statistical analysis of the historical event log data and potentially other patient-specific data being utilized to determine or otherwise assign probabilities of a specific event occurring based on the current operational context. In this regard, if the patient habitually engages in meals at or around a certain time of day, food intake gestures occurring at that time of day consistent with the patient's historical behavior may be more likely to be mapped to a meal event or other food intake event, or the detected meal event or food intake event may be assigned a higher probability or confidence value based on the consistency with the patient's historical behavior. Again, it should be noted that there are any number of different types of ancillary input data that may be correlative to the occurrence or non-occurrence of a particular event, and the subject matter described herein is not limited to any particular type or combination of ancillary inputs 607 that may be utilized by the event detection unit 606.

In one or more embodiments, the executable code or programming instructions corresponding to the event detection unit 606 is stored or otherwise maintained in a data storage element or memory, including any sort of short or long term storage media or other non-transitory computer-readable medium, which is capable of storing programming instructions for execution by a processor or other processing system. For example, in one or more exemplary embodiments, the computer-executable programming instructions corresponding to the event detection unit 606 are stored in a data storage element (e.g., memory 516) of a wearable electronic device including the sensor unit(s) 602, and, when read and executed by a processing system (e.g., controller 508) of the wearable electronic device, the instructions cause the wearable electronic device to generate the event detection unit 606 at the wearable electronic device. In this regard, in some embodiments, the wearable electronic device may transmit or otherwise provide signals or data indicating a stream of detected events and associated confidence or probability levels to another device for further processing and/or analysis. That said, in other embodiments, the event detection unit 606 may be implemented at or on a patient's mobile phone or other portable electronic device (e.g., user device 108) or on a cloud computing system or remote server that receives gesture data signals from the gesture recognition unit 604 implemented at another device via a network.

Still referring to FIG. 9, the patient management unit 608 generally represents a software application or component of the patient management system 600 that receives the detected event data from the event detection unit 606 and automatically initiates or otherwise performs one or more actions with respect to management of the patient's physiological condition. In some embodiments, the patient management unit 608 is configurable to support one or more autonomous operating modes for an infusion device, a smart pen, or other fluid delivery device, where the patient management unit 608 calculates or otherwise determines dosage commands for operating an actuation arrangement to deliver fluid to the patient. For example, in a closed-loop operating mode, the patient management unit 608 may determine a dosage command based at least in part on a current glucose measurement value for the patient in a manner that is influenced by an event detected by the event detection unit 606. In some embodiments, the patient management unit 608 is configurable to generate or otherwise provide user notifications or alerts via a user interface element based at least in part on a detected event. In this regard, the patient management 608 application may utilize patient-specific settings, preferences, or other notification criteria to automatically generate user notifications in a manner that is influenced by the detected event and potentially other factors (e.g., the patient's current or recent sensor glucose measurement values).

In one or more embodiments, the executable code or programming instructions corresponding to the patient management unit 608 is stored or otherwise maintained at one of the patient's associated devices (e.g., the patient's mobile phone, the patient's infusion device or other fluid delivery device, or the like) or at a cloud computing system or remote server. For example, the patient management unit 608 executing on the patient's phone may receive or otherwise obtain signals or data indicating detected gestures and/or events from the patient's smart watch or other wearable device, analyze the received data, and transmit or otherwise provide dosage commands or signals influenced by the detected gestured-based events to the patient's infusion device (e.g., via a wireless network) to automatically operate the infusion device to deliver insulin or another fluid or medicament to account for the detected event(s), or the patient management unit 608 may generate GUI displays or other user notifications influenced by the detected event(s) at the mobile device. That said, in other embodiments, when the patient management unit 608 is implemented at a remote server or other cloud computing system, the patient management unit 608 may transmit or otherwise provide dosage commands or signals to a device associated with the patient via a network. In yet other embodiments, the patient management unit 608 may be implemented at the patient's medical device and receive detected event data from the patient's mobile device, the patient's wearable device, or a remote server or other cloud computing system. In this regard, depending on the embodiment, the various units 604, 606, 608 may be distributed across one or more different devices 102, 103, 104, 106, 108, 111, 112, 114, 116 in a system 100 and the subject matter described herein is not limited to any particular implementation.

Figure 10:
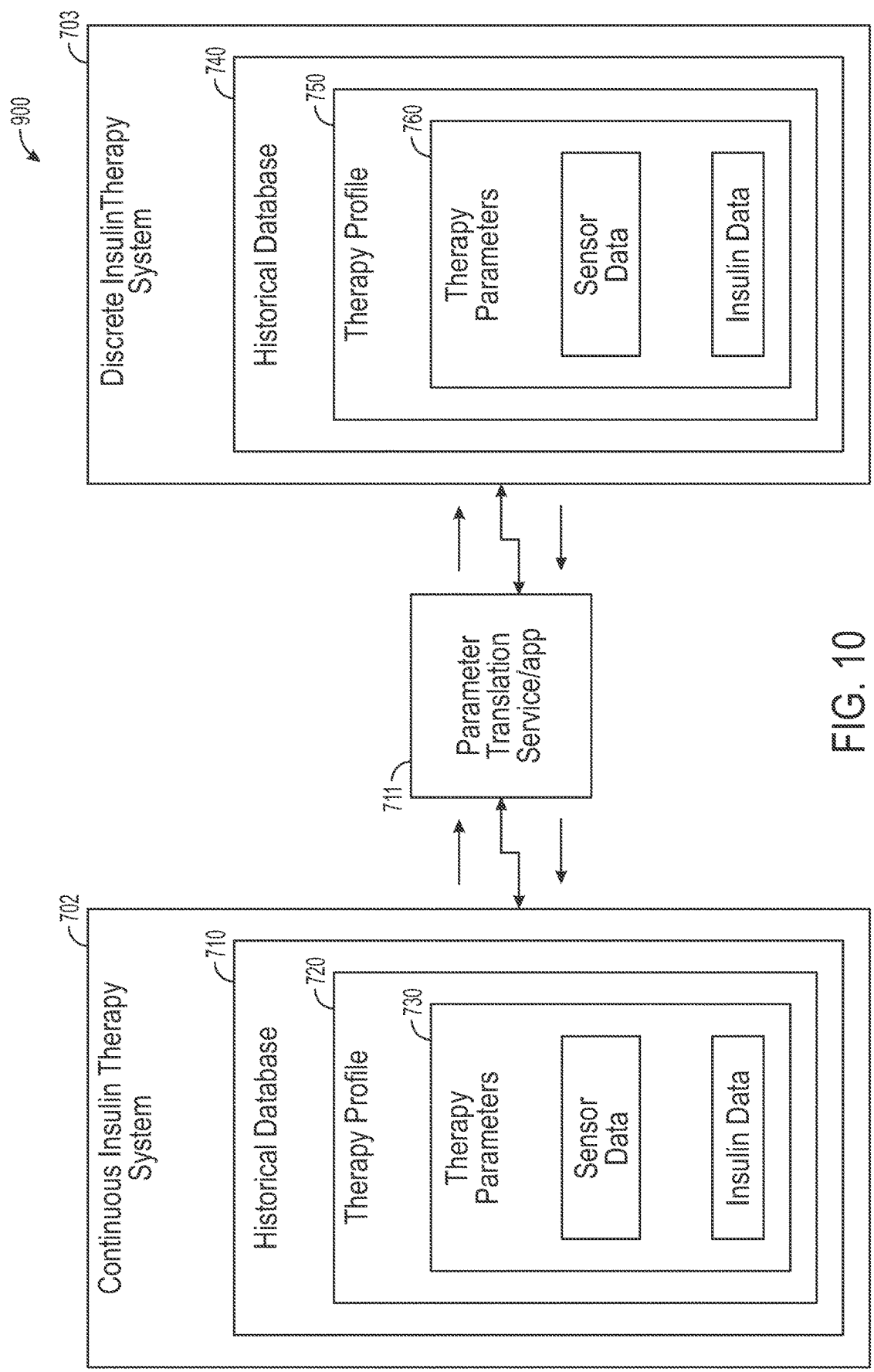
FIG. 10 is a block diagram illustrating a system in accordance with certain embodiments.

FIG. 10 is a block diagram illustrating a system 700 in accordance with certain embodiments. The system 700 includes a continuous insulin therapy system 702, a discrete insulin therapy system 703 and a parameter translation service (or application) 711 for translating therapy parameters of the continuous insulin therapy system 702 to translated therapy parameters for use at the discrete insulin therapy system 703, and vice-versa.

The implementation of the continuous insulin therapy system 702 can vary depending on the embodiment. For instance, continuous insulin therapy system 702 can be implemented using the continuous insulin therapy system 102 as described with respect to FIG. 1, the insulin infusion device 146 of FIG. 3A, or the insulin infusion device 402 of FIG. 7. In one embodiment, the continuous insulin therapy system 702 can include, for example, an insulin infusion device that regulates delivery of insulin to a user, and a glucose sensor to provide sensor data that indicates a glucose level of the user (e.g., a sensor augmented insulin pump). For instance, the continuous insulin therapy system 702 be implemented in conjunction with an analyte sensor (not illustrated in FIG. 10B), such as the analyte sensor 112 described with respect to FIG. 1, the glucose sensor system 408 described with respect to FIG. 7 and/or a continuous glucose monitoring device of FIG. 9. The insulin therapy system 702 is "continuous" in that it continuously measures a user's blood glucose levels and delivers insulin to the user.

The continuous insulin therapy system 702 includes a historical database 710 that stores one or more therapy profiles 720 for a user of the continuous insulin therapy system 702. Each therapy profile 720 can include therapy parameters 730 including sensor data and insulin data, settings for the continuous insulin therapy system 702, and control algorithms implemented by the continuous insulin therapy system 702.

By contrast, the discrete insulin therapy system 703 is different than the continuous insulin therapy system. In one embodiment, the discrete insulin therapy system 703 can be implemented as an insulin injection pen system that includes one or more insulin pens. For example, one insulin pen can be used to discretely inject long acting insulin, and another insulin pen can be used to discretely inject rapid acting insulin. The insulin therapy system 703 is "discrete" in that it can be used to discretely deliver insulin to the user.

The implementation of the discrete insulin therapy system 703 can vary depending on the embodiment. For instance, the discrete insulin therapy system 703 can be implemented the smart insulin pen 160 described with respect to FIG. 3B, the smart pen accessory 170 described with respect to FIG. 4, or the injection pen 200 described with respect to FIG. 5. In some embodiments, the discrete insulin therapy system 703 can also include a sensor that is used in conjunction with a pen to provide a user with information regarding their blood glucose levels. For example, the discrete insulin therapy system 703 can be implemented in conjunction with an analyte sensor, such as the analyte sensor 112 described with respect to FIG. 1, the glucose sensor system 408 described with respect to FIG. 7 and/or a continuous glucose monitoring device of FIG. 9. Information provided by the sensor regarding the user's blood glucose levels can be discrete or continuous measurements. In some embodiments, the discrete insulin therapy system 703 can also include a user device having a health care application, such as the user device 108 described above with reference to FIG. 1. The user device can be used in conjunction with an insulin injection pen, and optionally an analyte sensor, to communicate with other systems that are external to the discrete insulin therapy system 703.

Referring again to FIG. 10, similar to the continuous insulin therapy system 702, the discrete insulin therapy system 703 includes a historical database 740 that stores one or more therapy profiles 750 for a user of the discrete insulin therapy system 703. Each therapy profile 750 can include therapy parameters 760 including sensor data and insulin data, settings for the discrete insulin therapy system 703, and control algorithms implemented by the discrete insulin therapy system 703. In some examples, historical database 740 may be stored on a smart insulin pen (e.g., smart insulin pen 160 of FIG. 3B), a smart insulin pen cap (e.g., smart pen accessory 170 of FIG. 4), and/or on user device (computer-based or processor-based device 300 of FIG. 6).

The continuous insulin therapy system 702 can send a therapy profile 750 to the translation service 711. The therapy profile 750 includes one or more therapy parameters 760. Non-limiting examples of therapy parameters 760 can include a basal profile, an active insulin time, an insulin sensitivity factor of the user, an insulin-to-carbohydrate ratio for the user (or alternatively the carbohydrate-to-insulin ratio for the user), and/or a total daily dose of insulin delivered to the user.

As used herein, the term "basal insulin" can refer to a therapy setting for an insulin infusion device that specifies an hourly, continuous infusion of insulin delivered automatically by an insulin infusion device based on preprogrammed profiles and personalized rates set in the insulin infusion device. The insulin infusion device delivers a daily infusion of insulin that typically covers "background" insulin needs during periods of fasting (e.g., overnight and between meals). The basal profile can include at least one basal rate setting for the user that indicates a rate of continuous insulin infusion delivered to the user to keep blood glucose of the user stable during fasting periods. As used herein, the term "basal rate" can refer to a therapy setting for an insulin infusion device that provides a delivery rate that indicates a continuous infusion of insulin to keep blood glucose stable, for example, between meals and during the night for a specific patient. Basal insulin mimics pancreatic insulin delivery, which meets all the body's non-food related insulin needs. A basal rate profile can define a plurality of basal rates corresponding to a plurality of time segments (e.g., during a 24-hour day). As used herein, the term "a maximum basal rate" can refer to a therapy setting for an insulin infusion device that specifies a maximum amount of basal insulin that an insulin infusion device should deliver at one time for a specific patient.

As used herein, the term "active insulin" or "insulin on board (IOB)" can refer to bolus insulin that has been delivered to a user's body, but that has not yet been used by the patient. For example, active insulin can refer to how much insulin is still active inside the body from the previous bolus dose. Stated differently, the active insulin time can indicate an amount of time a bolus of insulin remains active in a user after injection. As used herein, the term "active insulin time" can refer to a therapy setting for an insulin infusion device that specifies a duration of insulin action in a specific user's body, or an amount of time insulin remains working in a specific user's body after a bolus of rapid acting insulin. Active insulin time (sometime also referred to as duration of insulin action (DIA)) can refer to how long a bolus of insulin takes to be absorbed by a user's body and finish lowering blood glucose. The time starts when a bolus is given and ends when the bolus is no longer lowering blood glucose levels. An accurate active insulin time can help minimize insulin stacking and low blood sugar (hypoglycemia), which can happen when boluses are given too close together. Active insulin time varies from person to person. As used herein, the term "a maximum bolus limit" can refer to a therapy setting for an insulin infusion device that specifies a maximum amount of bolus insulin that an insulin infusion device should deliver at one time for a specific patient.

As used herein, the term "insulin sensitivity factor (ISF)" or "correction factor" can refer to a therapy setting for an insulin infusion device that specifies an amount that a specific user's blood glucose (BG) level (e.g., in mg/dL or mmol/L) is reduced by one unit of insulin. In other words, ISF can indicate how much one unit of insulin is expected to lower blood sugar, and can describe the amount of bolus that is delivered per 1 mg/dL deviation of glucose from a target glucose value.

As used herein, the term "insulin-to-carbohydrate ratio" can refer to a therapy setting for an insulin infusion device that specifies an amount of insulin required to cover a given number of carbohydrates. For instance, the insulin-to-carbohydrate ratio can indicate an amount of bolus insulin that is delivered per one unit of carbohydrate intake. In other words, insulin-to-carbohydrate ratio can refer to the number of grams of carbohydrates "covered" by one unit of insulin. By contrast, the carbohydrate-to-insulin ratio for a user indicates a ratio of an amount of carbohydrates in grams covered by one unit of insulin.

As used herein, the term "total daily dose" (or TDD) can refer to a number on insulin units that a user of an insulin infusion device uses (e.g., on average) per day. The total daily dose of insulin can be computed based on the total basal insulin delivered to the user and total bolus insulin delivered to the user. As used herein, the term "bolus insulin" can refer to a therapy setting for an insulin infusion device that specifies a dose of insulin for a specific patient that is needed to cover an expected rise in blood glucose (such as the rise after a meal or a snack) or to lower a high blood glucose down to target range. Target blood glucose or "target range" is a setting that indicates a desired blood glucose level. It can be entered into an insulin infusion device as a single target for the entire day (e.g., 120 mg/dl) or as a range (e.g., 100-120 mg/dl). Many insulin infusion devices have a built-in bolus calculator that calculates how much insulin to take for a meal or for correcting blood sugars. Bolus calculator settings can include: target blood glucose/range; insulin-to-carbohydrate ratio (I:C) or carbohydrate-to-insulin ratio (C:I); insulin sensitivity factor (ISF) or correction factor; active insulin time or duration of insulin action (DIA), and insulin on board (IOB).

For example, the total daily dose may be computed using insulin delivery data, including basal insulin and insulin bolus amounts, along with their associated time data (time/date stamps). The total daily dose can be used to compute the patient's insulin sensitivity factor (ISF), which is expressed in mg/dL/Unit, and/or insulin-to-carbohydrate ratio.

The parameter translation service 711 can translate the therapy parameters 730 from the therapy profile 720 into translated therapy parameters that are mapped to and adapted for use by the discrete insulin therapy system 703 (e.g., therapy parameters 760). For example, the parameter translation service 711 can map a basal rate setting for the user to a number of long acting insulin units to be injected by the user (via an insulin pen) and timing recommendations for injection of the long acting insulin units. The parameter translation service 711 can also map the insulin sensitivity factor of the user to a number of rapid acting insulin units to be injected by the user (via an insulin pen) during periods of elevated glucose. The parameter translation service 711 can also map the carbohydrate-to-insulin ratio for the user to a number of rapid acting insulin units to be injected by the user (via an insulin pen) before consuming a particular amount of carbohydrates taking a difference between basal rate and long acting insulin into account, etc.

The translated therapy parameter(s) can then be sent to the discrete insulin therapy system 703 for use at the discrete insulin therapy system 703. Settings of the discrete insulin therapy system 703 can be configured in accordance with the translated therapy parameter(s). In some embodiments, one or more settings to be applied at the discrete insulin therapy system 703 can be generated based on the translated therapy parameter(s), and an instruction to apply the one or more settings can be communicated to the discrete insulin therapy system 703 for use at the discrete insulin therapy system 703. The translated therapy parameter(s) and/or the one or more settings can be applied at a controller of the discrete insulin therapy system 703 to control insulin delivery by the discrete insulin therapy system 703. For example, the number of long acting insulin units to be injected by the user and timing recommendations for injection can be adjusted (e.g., based on the time of day, day of the week, day of the month, time of the year, or other cyclical behavior). Alternatively, or additionally, rapid dosing parameters can be adjusted by setting the number of rapid acting insulin units to be injected by the user during periods of elevated glucose, and/or by setting the number of rapid acting insulin units to be injected by the user before consuming a particular amount of carbohydrates.

Similarly, the discrete insulin therapy system 703 can send a therapy profile 750 to the translation service 711 that includes one or more therapy parameters 760. Non-limiting examples of therapy parameters 760 can include a number of long acting insulin units to be injected by the user and timing recommendations for injection of the long acting insulin units, a number of rapid acting insulin units to be injected by the user during periods of elevated glucose, another number of rapid acting insulin units to be injected by the user before consuming a particular amount of carbohydrates, an active insulin time, an insulin sensitivity factor of the user, a carbohydrate-to-insulin ratio for the user, a total daily dose of insulin delivered to the user, and the like. In some embodiments, some, but not all, of the therapy parameters 760, such as the active insulin time, the insulin sensitivity factor of the user, and the carbohydrate-to-insulin ratio for the user, can be optimized by the discrete insulin therapy system 703 prior to sending them to the parameter translation service 711 and no further optimization needs to be performed by the parameter translation service 711. However, in other embodiments, the active insulin time, the insulin sensitivity factor of the user, and the carbohydrate-to-insulin ratio for the user, are not optimized by the discrete insulin therapy system 703 and further optimization needs to be performed by an optimization process (not shown) that can be implemented at the parameter translation service 711.

The parameter translation service 711 can translate the therapy parameters 760 from the therapy profile 750 into translated therapy parameters that are mapped to and adapted for use by the continuous insulin therapy system 702. For example, the parameter translation service 711 can map the number of long acting insulin units and the timing recommendations for injection to a basal profile. The basal profile can include at least one basal rate setting for the user that indicates a rate of continuous insulin infusion delivered to the user to keep blood glucose of the user stable (e.g., during fasting periods). The parameter translation service 711 can also map the number of rapid acting insulin units to be injected by the user (via an insulin pen) during periods of elevated glucose to an insulin sensitivity factor of the user (e.g., that indicates an amount that blood glucose of the user is reduced by one unit of insulin). As another example, the parameter translation service 711 can also map the number of rapid acting insulin units to be injected by the user (via an insulin pen) before consuming a particular amount of carbohydrates to a carbohydrate-to-insulin ratio for the user that indicates a ratio of an amount of carbohydrates in grams covered by one unit of insulin. The translated therapy parameter(s) can then be sent to the continuous insulin therapy system 702 for use at the continuous insulin therapy system 702. In one embodiment, one or more settings to be applied at the continuous insulin therapy system 702 can be generated based on the translated therapy parameter(s), and an instruction to apply the one or more settings can be communicated to the continuous insulin therapy system 702 for use at the continuous insulin therapy system 702. Regardless of the implementation, one or more settings of the continuous insulin therapy system 702 can be automatically configured in accordance with the translated therapy parameter(s). This can include applying settings at a controller of the continuous insulin therapy system to control insulin delivery by the continuous insulin therapy system 702.

Figure 11:
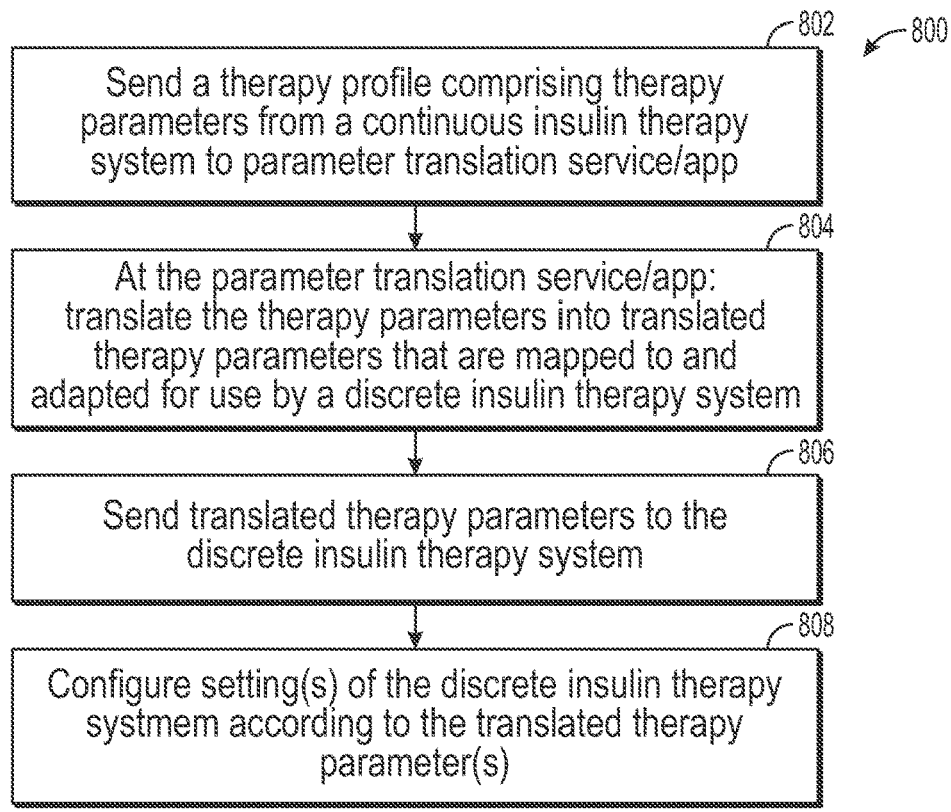
FIG. 11 is a flowchart illustrating a method for translating one or more therapy parameters of a continuous insulin therapy system to one or more translated therapy parameters for use at a discrete insulin therapy system in accordance with certain embodiments.

FIG. 11 is a flowchart illustrating a method 800 for translating one or more therapy parameters 730 of a continuous insulin therapy system 702 to one or more translated therapy parameters for use at a discrete insulin therapy system 703 in accordance with certain embodiments. The method 800 starts at 802, where a therapy profile 720 generated at a continuous insulin therapy system 702 is sent to a parameter translation service 711. The continuous insulin therapy system 702 can include, for example, an insulin infusion device that regulates delivery of insulin to a user, and a glucose sensor to provide sensor data that indicates a glucose level of the user (e.g., a sensor augmented insulin pump). The therapy profile 720 includes one or more therapy parameters 730. Non-limiting examples of therapy parameters 730 can include a basal profile, an active insulin time, an insulin sensitivity factor of the user, a carbohydrate-to-insulin ratio for the user, a total daily dose of insulin delivered to the user, and the like. The basal profile can include at least one basal rate setting for the user that indicates a rate of continuous insulin infusion delivered to the user to keep blood glucose of the user stable during fasting periods. The active insulin time indicates an amount of time a bolus of rapid acting insulin remains active in the user after injection. The insulin sensitivity factor of the user indicates an amount that blood glucose of the user is reduced by one unit of insulin. The carbohydrate-to-insulin ratio for the user indicates a ratio of an amount of carbohydrates in grams covered by one unit of insulin. The total daily dose of insulin comprising total basal insulin delivered to the user and total bolus insulin delivered to the user.

At 804, the parameter translation service 711 can translate at least one of the therapy parameters 730 from the therapy profile 720 into at least one translated therapy parameter. The translated therapy parameter(s) can be mapped to and adapted for use by the discrete insulin therapy system 703 that is different than the continuous insulin therapy system (e.g., insulin injection pen system that includes one or more pens used to discretely inject long acting insulin and/or rapid acting insulin). For example, the parameter translation service 711 can map a basal rate setting for the user to a number of long acting insulin units to be injected by the user and timing recommendations for injection of the long acting insulin units, can map the insulin sensitivity factor of the user to a number of rapid acting insulin units to be injected by the user during periods of elevated glucose, can map the carbohydrate-to-insulin ratio for the user to a number of rapid acting insulin units to be injected by the user before consuming a particular amount of carbohydrates taking a difference between basal rate and long acting insulin into account, etc. In some embodiments, some, but not all, of the therapy parameters 730, such as the active insulin time, the insulin sensitivity factor of the user, and the carbohydrate-to-insulin ratio for the user, can be optimized by the continuous insulin therapy system 702 prior to sending them to the parameter translation service 711 and no further optimization needs to be performed by the parameter translation service 711. However, in other embodiments, the active insulin time, the insulin sensitivity factor of the user, and the carbohydrate-to-insulin ratio for the user, are not optimized by the continuous insulin therapy system 702 and further optimization needs to be performed by an optimization process (not shown) that can be implemented at the parameter translation service 711.

At 806, the translated therapy parameter(s) can then be sent to the discrete insulin therapy system 703 for use at the discrete insulin therapy system 703. In one embodiment, when the discrete insulin therapy system 703 has communication interfaces that allow it to communicate with the parameter translation service 711, the translated therapy parameter(s) can then be sent directly to the discrete insulin therapy system 703 from the parameter translation service 711. In another embodiment, the translated therapy parameter(s) can be sent to the discrete insulin therapy system 703 indirectly via an intermediary device, such as a user device 108 of FIG. 1 for example, that is in communication with other external systems including one that can host the parameter translation service 711. At 808, one or more settings of the discrete insulin therapy system 703 can be configured in accordance with the translated therapy parameter(s). For example, the number of long acting insulin units to be injected by the user and timing recommendations for injection of the long acting insulin units can be adjusted (e.g., based on the time of day, day of the week, day of the month, time of the year, or other cyclical behavior). Alternatively, or additionally, rapid dosing parameters can be adjusted by setting the number of rapid acting insulin units to be injected by the user during periods of elevated glucose, or setting the number of rapid acting insulin units to be injected by the user before consuming a particular amount of carbohydrates. In addition, in some embodiments, settings can be applied at a controller of the discrete insulin therapy system 703 to control insulin delivery by the discrete insulin therapy system 703 (e.g., to prepare a particular number of insulin units or a bolus amount for injection).

Figure 12:
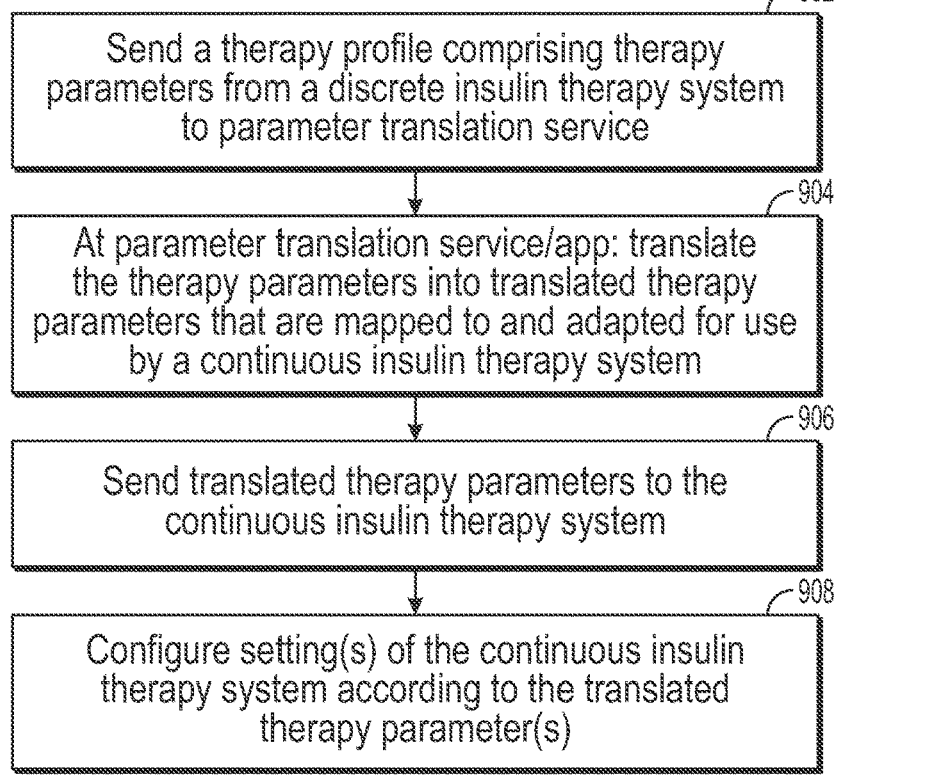
FIG. 12 is a flowchart illustrating a method for translating one or more therapy parameters of a discrete insulin therapy system to one or more translated therapy parameters for use at a continuous insulin therapy system in accordance with certain embodiments.

FIG. 12 is a flowchart illustrating a method 900 for translating one or more therapy parameters 760 of a discrete insulin therapy system 703 to one or more translated therapy parameters for use at a continuous insulin therapy system 702 in accordance with certain embodiments. The method 900 starts at 902, where a therapy profile 750 generated at a discrete insulin therapy system 703 is sent to a translation service 711. The therapy profile 750 includes one or more therapy parameters 760. Non-limiting examples of therapy parameters 760 can include a number of long acting insulin units to be injected by the user and timing recommendations for injection of the long acting insulin units, a number of rapid acting insulin units to be injected by the user during periods of elevated glucose, another number of rapid acting insulin units to be injected by the user before consuming a particular amount of carbohydrates, an active insulin time, an insulin sensitivity factor of the user, a carbohydrate-to-insulin ratio for the user, and a total daily dose of insulin delivered to the user. In some embodiments, some, but not all, of the therapy parameters 760, such as the active insulin time, the insulin sensitivity factor of the user, and the carbohydrate-to-insulin ratio for the user, can be optimized by the discrete insulin therapy system 703 prior to sending them to the parameter translation service 711 and no further optimization needs to be performed by the parameter translation service 711. However, in other embodiments, the active insulin time, the insulin sensitivity factor of the user, and the carbohydrate-to-insulin ratio for the user, are not optimized by the discrete insulin therapy system 703 and further optimization needs to be performed by an optimization process (not shown) that can be implemented at the parameter translation service 711.

At 904, the parameter translation service 711 can translate at least one of the therapy parameters 760 from the therapy profile 750 into at least one translated therapy parameter. The translated therapy parameter is mapped to and adapted for use by the continuous insulin therapy system 702. For example, the parameter translation service 711 can map the number of long acting insulin units and the timing recommendations for injection to a basal profile. The basal profile can include at least one basal rate setting for the user that indicates a rate of continuous insulin infusion delivered to the user to keep blood glucose of the user stable (e.g., during fasting periods). The parameter translation service 711 can also map the number of rapid acting insulin units to be injected by the user during periods of elevated glucose to an insulin sensitivity factor of the user (e.g., that indicates an amount that blood glucose of the user is reduced by one unit of insulin). As another example, the parameter translation service 711 can also map the number of rapid acting insulin units to be injected by the user before consuming a particular amount of carbohydrates to a carbohydrate-to-insulin ratio for the user that indicates a ratio of an amount of carbohydrates in grams covered by one unit of insulin.

At 906, the translated therapy parameter(s) can be sent to the continuous insulin therapy system 702 for use at the continuous insulin therapy system 702. At 908, one or more settings of the continuous insulin therapy system 702 can be automatically configured in accordance with the translated therapy parameter(s). For example, this can include applying the settings at a controller of the continuous insulin therapy system 702 to control insulin delivery by the continuous insulin therapy system 702.

Figure 13:
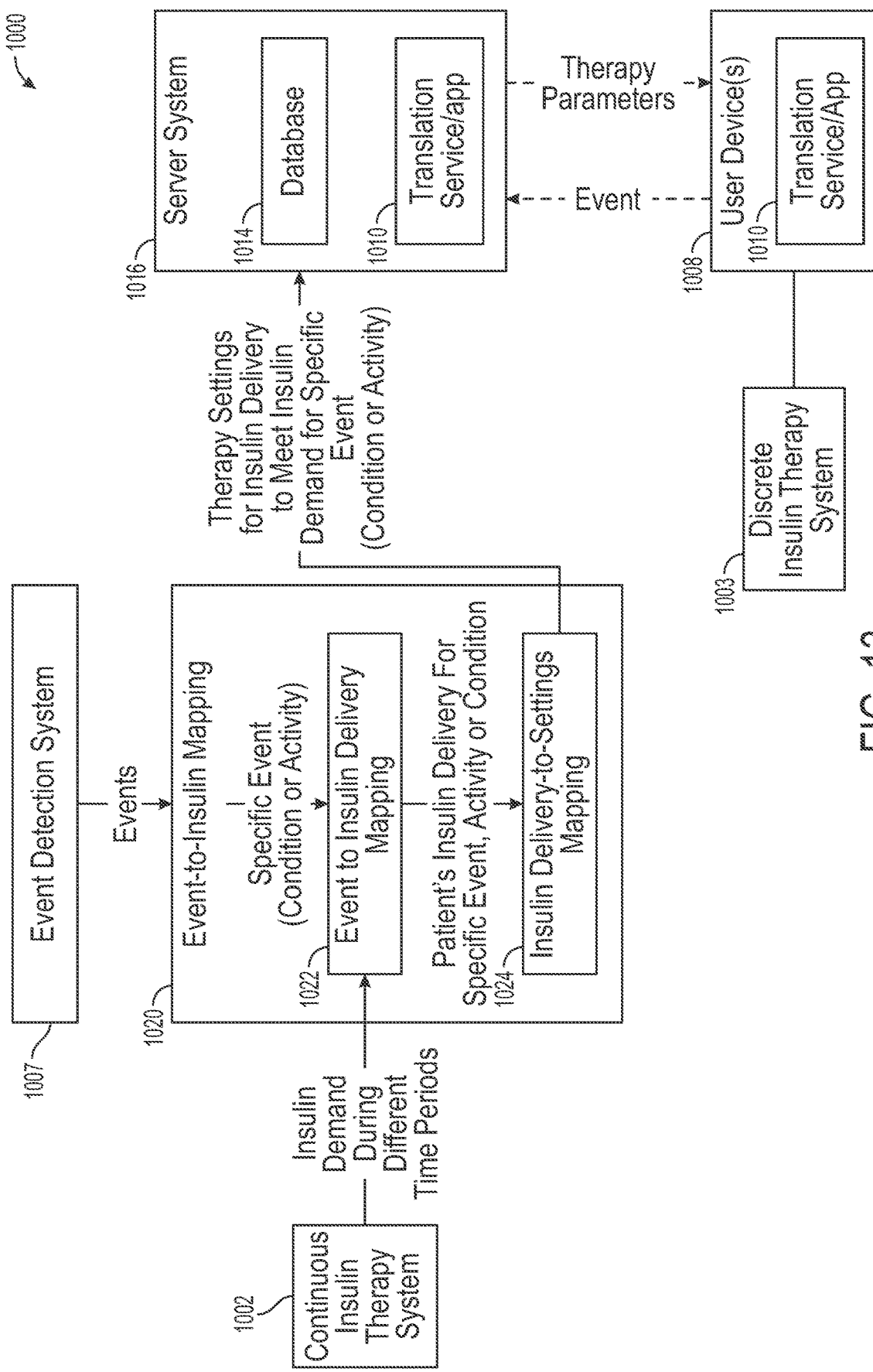
FIG. 13 is a block diagram illustrating a system in accordance with certain embodiments.

FIG. 13 is a block diagram illustrating a system 1000 in accordance with certain embodiments. The system 1000 includes a continuous insulin therapy system 1002, an event detection system 1007, an event-to-insulin mapping service 1020, a server system including a parameter translation service (or app) 1011 and a database 1014, a user device 1008, and a discrete insulin therapy system 1003. The parameter translation service (or app) 1011 can be used for translating therapy parameters of the continuous insulin therapy system 1002 to translated therapy parameters for use at the discrete insulin therapy system 1003. In the embodiment illustrated in FIG. 13, the parameter translation service (or app) 1011, can be implemented at the server system 1016 and/or at the user device 1008. However, depending on the implementation, the parameter translation service (or app) 1011 can also be implemented at the continuous insulin therapy system 1202 or at another computer-based system that is distinct from the server system 1016

The implementation of the continuous insulin therapy system 1002 can vary depending on the embodiment. For instance, continuous insulin therapy system 1002 can be implemented using the continuous insulin therapy system 102 as described with respect to FIG. 1, the insulin infusion device 146 of FIG. 3A, or the insulin infusion device 402 of FIG. 7. In one embodiment, the continuous insulin therapy system 1002 can include, for example, an insulin infusion device that regulates delivery of insulin to a user, and a glucose sensor to provide sensor data that indicates a glucose level of the user (e.g., a sensor augmented insulin pump). For instance, the continuous insulin therapy system 1002 be implemented in conjunction with an analyte sensor (not illustrated in FIG. 10B), such as the analyte sensor 112 described with respect to FIG. 1, the glucose sensor system 408 described with respect to FIG. 7 and/or a continuous glucose monitoring device of FIG. 9. The insulin therapy system 1002 is "continuous" in that it continuously measures a user's blood glucose levels and delivers insulin to the user.

By contrast, the discrete insulin therapy system 1003 is different than the continuous insulin therapy system. In one embodiment, the discrete insulin therapy system 1003 can be implemented as an insulin injection pen system that includes one or more insulin pens. For example, one insulin pen can be used to discretely inject long acting insulin, and another insulin pen can be used to discretely inject rapid acting insulin. The insulin therapy system 1003 is "discrete" in that it discretely delivers insulin to the user.

The implementation of the discrete insulin therapy system 1003 can vary depending on the embodiment. For instance, the discrete insulin therapy system 1003 can be implemented the smart insulin pen 160 described with respect to FIG. 3B, the smart pen accessory 170 described with respect to FIG. 4, or the injection pen 200 described with respect to FIG. 5. In some embodiments, the discrete insulin therapy system 1003 can also include a sensor that is used in conjunction with a pen to provide a user with information regarding their blood glucose levels. For example, the discrete insulin therapy system 1003 can be implemented in conjunction with an analyte sensor, such as the analyte sensor 112 described with respect to FIG. 1, the glucose sensor system 408 described with respect to FIG. 7 and/or a continuous glucose monitoring device of FIG. 9. Information provided by the sensor regarding the user's blood glucose levels can be discrete or continuous measurements. In some embodiments, the discrete insulin therapy system 1003 can also include a user device having a health care application, such as the user device 108 described above with reference to FIG. 1. The user device can be used in conjunction with an insulin injection pen, and optionally an analyte sensor, to communicate with other systems that are external to the discrete insulin therapy system 1003.

The continuous insulin therapy system 1002 can provide therapy parameters including sensor data and insulin data, settings for the continuous insulin therapy system 1002, and control algorithms implemented by the continuous insulin therapy system 1002 to the event-to-insulin mapping service 1020. The insulin data can include information that describes a user's insulin demand during different time periods.

Depending on the implementation, the event detection system 1007 and the event-to-insulin mapping service 1020 can be implemented at the server system 1016, at the user device 1008, at the continuous insulin therapy system 1002 or at another computer-based system that is distinct from the server system 1016, and therefore are illustrated as separate block 1220 to account for any of those implementations.

The event detection system 1007 can include, for example, components of the event detection system 107 described with respect to FIG. 1, the gesture-based event detection system 500 described with respect to FIG. 8, the gesture-informed patient management system 600 described with respect to FIG. 9. These devices and systems are described above, and for sake of brevity, a detailed description of these devices and systems will not be repeated.

The event detection system 1007 can detect various events associated with a user. As used herein, an "event" can refer to a specific condition or activity that is detectable and indicative of a physical behavior of a user (or that is associated with a physical behavior of a user). Each event can potentially impact physiological glucose dynamics of the user and can be correlated to a change in an insulin demand of the user and/or blood glucose levels of the user. Non-limiting examples of events can include, but are not limited: meal ingestion events including timing, meal content, and meal duration; a sleep event including timing and duration; a physical activity event including exertion, timing and duration (e.g., an exercise event), and a work-related event including timing and duration. Any of these events can be input by a user, measured or detected by a sensor-based system, or estimated or predicted by a model or system, such as a mathematical model or artificial intelligence (AI) based system. In addition, any of these events can be recorded in a database and later used for the various purposes described herein.

In some cases, events can include, for example, events from an insulin therapy system such as therapy-related data associated with operation of the insulin infusion device. Therapy-related data can include data related to the status of the infusion device and/or the status of the user. Some non-limiting examples of therapy-related data can include, but are not limited to: sensor glucose data associated with glucose levels of the user; meal data associated with meals announced by the user; insulin delivery data, including basal insulin and insulin bolus amounts, along with their associated time data (time/date stamps); announced meal time data or information; carbohydrate intake data for a user including carbohydrate intake estimates for announced meals; the insulin sensitivity factor (ISF) associated with operation of the device in the manual insulin delivery mode; an insulin to carbohydrate ratio (ICR) value; and user-entered blood glucose meter measurements. The therapy-related data can also include, for example, closed-loop pump data including, but not limited to: settings from an insulin infusion device of a user; data indicating basal insulin delivered by the insulin infusion device to the user during operation in the automated closed-loop insulin delivery mode for at least one defined period of time; data that indicates the total amount of insulin delivered by the infusion device during at least one defined period of time (e.g., the last 24 hours, a number of sequential segments of time, etc.), such as the average total daily dose (TDD) of insulin for the user; glucose sensor data, log data for the infusion device, user-input data, time/calendar data associated with certain events or collected data, and/or other information.

Events can also include many other types of information, and can be detected or be determined based on various types of data from detection systems or devices, such as an activity tracker device. Examples of such data can include, but not limited to: accelerometer (x,y,z) data, geolocation data, iBeacon location data, skin temperature data, ambient air temperature data, bioimpedance heart rate data, sweat data (e.g., GSR-conductance), blood pressure data, shake detection data, pedometer data, barometer data, gyroscope data, meal log data, orientation data (e.g., azimuth, pitch, roll (degrees)); health kit data (such as data from Apple® Healthkit, Google® Fit, etc.), medication/prescription information data, user gestures data, UV light detector data, magnetometer data, respiration data, muscle activity data, pulse oximeter data, blood and interstitial fluid pH data, METS data, sleep quality/time data, EMR and lab data, etc.

In some cases, an event (or impact of that physical behavior) can potentially impact physiological glucose dynamics of the user. An event can be correlated, for example, to a change in one or more of an insulin demand of the user and/or blood glucose levels of the user. An event (or combination of events) can be associated with a probability of a decreased insulin delivery demand or an increased insulin delivery demand for that event (or particular combination of events). In some cases, an event (or combination of events) can be correlated to: a decreased insulin delivery demand when the probability of the decreased insulin delivery demand is greater than a first threshold; an increased insulin delivery demand when the probability of the increased insulin delivery demand is greater than a second threshold; or an ordinary insulin delivery demand when the probability of the decreased insulin delivery demand is less than the first threshold and the probability of the increased insulin delivery demand is less than the second threshold.

In some cases, insulin delivery demand can be associated with a predicted glycemic outcome. For instance, in some cases, the insulin delivery demand can be associated with a predicted glycemic outcome that indicates: a probability of an upcoming hyperglycemic condition that would increase insulin delivery demand when the probability is greater than or equal to a threshold, or a probability of an upcoming hypoglycemic condition that would reduce insulin delivery demand when the probability is greater than or equal to another threshold. In other cases, the insulin delivery demand is not associated with a predicted glycemic outcome.

Referring again to FIG. 13, information about each event and the timing thereof can be provided to the continuous insulin therapy system 1002, the server system 1016, the user device 1008, the discrete insulin therapy system 1003, and/or to the event-to-insulin mapping service 1020. In one embodiment, in response to each event that is detected, the event-to-insulin mapping service 1020 can determine an insulin delivery profile for the continuous insulin therapy system 1002 during a period following occurrence of the event. The insulin delivery profile comprises therapy parameters for the continuous insulin therapy system 1002 to provide insulin delivery in accordance with the insulin delivery profile during the period following the event. The therapy parameters can include therapy settings for insulin delivery to meet insulin demand in response to the specific event (e.g., condition or activity). Non-limiting examples of the therapy parameters can include, but are not limited to: a basal profile comprising basal rate parameters and type and dosage of basal insulin; bolus data comprising type, dosage and timing of bolus insulin to meet insulin demand in response to the event; an active insulin time; an insulin sensitivity factor; a carbohydrate-to-insulin ratio, etc.

The event-to-insulin mapping service 1020 can map the detected event to the insulin delivery profile. The event-to-insulin mapping service 1020 can then map therapy parameters to translated therapy parameters for the discrete insulin therapy system 1003. When operated in accordance with the translated therapy parameters the discrete insulin therapy system 1003 can provide insulin delivery in accordance with the insulin delivery profile (that was determined at 1104). The mapping of the event to the translated therapy parameters can be stored in a database 1014. The discrete insulin therapy system 1003 can then use the translated therapy parameters to deliver insulin to the user to provide insulin delivery in accordance with the insulin delivery profile and satisfy an insulin delivery demand associated with that event. Non-limiting examples of the translated therapy parameters can include, but are not limited to: a total daily dosage of insulin; type, dosage and timing of long-lasting insulin to be injected in response to the event as determined based on the basal profile; type, dosage and timing of rapid acting insulin to be injected in response to the event (as determined based on the bolus data to meet insulin demand for the event); the active insulin time; the insulin sensitivity factor; the carbohydrate-to-insulin ratio, etc.

When a user device 1008 receives an in indication that the event is subsequently detected, the translation service 1011 can retrieve translated therapy parameters for the discrete insulin therapy system 1003 and present them via a user interface the user device 1008 and/or the discrete insulin therapy system 1003. The translated therapy parameters for the discrete insulin therapy system 1003 can include recommended settings for the discrete insulin therapy system 1003. The discrete insulin therapy system 1003 can be configured according to the translated therapy parameters and/or recommended settings. For instance, the settings can be applied at a controller of the discrete insulin therapy system 1003 to control insulin delivery by the discrete insulin therapy system 1003.

Figure 14:
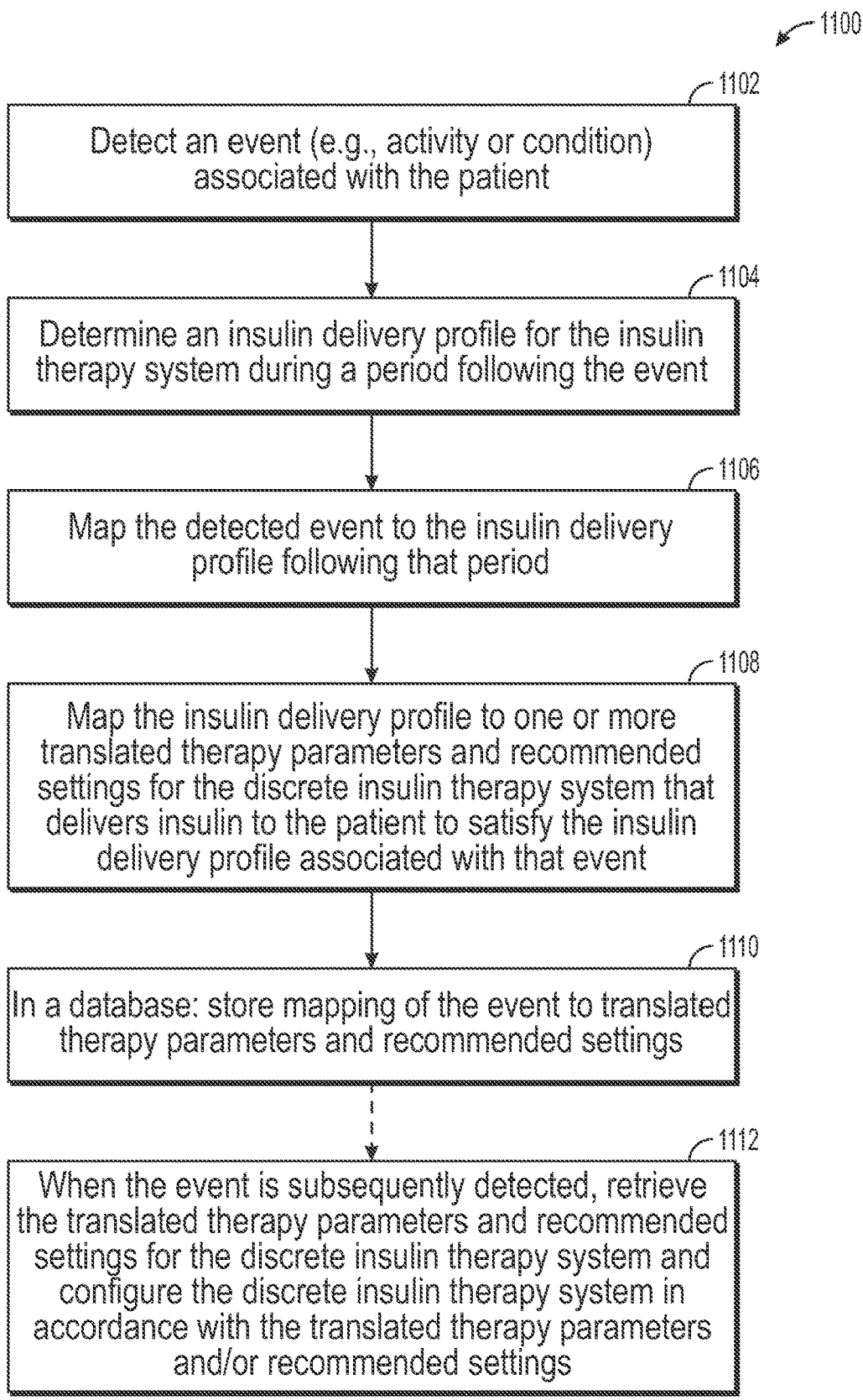
FIG. 14 is a flowchart illustrating a method for translating therapy parameters of a continuous insulin therapy system to translated therapy parameters for use at a discrete insulin therapy system in accordance with certain embodiments.

FIG. 14 is a flowchart illustrating a method 1100 for translating therapy parameters of a continuous insulin therapy system 702 to translated therapy parameters for use at a discrete insulin therapy system 703 in accordance with certain embodiments. The event-to-insulin mapping service 1020 can regularly determine an insulin delivery profile for the continuous insulin therapy system 1002. The insulin delivery profile can vary over time. The insulin delivery profile comprises therapy parameters for the continuous insulin therapy system 1002 to provide insulin delivery (in accordance with the insulin delivery profile). The therapy parameters can include therapy settings for insulin delivery to meet insulin demand in response to the specific event (e.g., condition or activity). Non-limiting examples of the therapy parameters can include, but are not limited to: a basal profile comprising basal rate parameters and type and dosage of basal insulin; bolus data comprising type, dosage and timing of bolus insulin to meet insulin demand in response to the event; an active insulin time; an insulin sensitivity factor; a carbohydrate-to-insulin ratio, etc.

The method 1100 starts at 1102, where an event detection system detects an event associated with a user. The event can be a specific condition or activity that is indicative of a physical behavior of the user. The event can potentially impact physiological glucose dynamics of the user and is correlated to a change in an insulin demand of the user and/or blood glucose levels of the user. Non-limiting examples of events can include, but are not limited to a meal ingestion event, a sleep event, a physical activity event, an exercise event and a work-related event.

At 1104, the event-to-insulin mapping service 1020 can determine an insulin delivery profile for the continuous insulin therapy system 1002 during a period following the event. The insulin delivery profile comprises therapy parameters for the continuous insulin therapy system 1002 to provide insulin delivery (in accordance with the insulin delivery profile) during the period following the event that was detected at 1102.

At 1106, the event-to-insulin mapping service 1020 can map the detected event to the insulin delivery profile during the period following the event. At 1108, the event-to-insulin mapping service 1020 can map therapy parameters to translated therapy parameters for the discrete insulin therapy system 1003. The translated therapy parameters can be applied at the discrete insulin therapy system 1003 to deliver insulin in accordance with the insulin delivery profile. This can allow the discrete insulin therapy system 1003 to deliver insulin to the user to provide insulin delivery in accordance with the insulin delivery profile and satisfy an insulin delivery demand associated with that event. At 1110, the mapping of the event to the translated therapy parameters can be stored in a database. Non-limiting examples of the translated therapy parameters can include, but are not limited to: a total daily dosage of insulin; type, dosage and timing of long-lasting insulin to be injected in response to the event as determined based on the basal profile; type, dosage and timing of rapid acting insulin to be injected in response to the event as determined based on the bolus data to meet insulin demand for the event; the active insulin time; the insulin sensitivity factor; the carbohydrate-to-insulin ratio, etc.

When the event is subsequently detected, at 1112, the translated therapy parameters for the discrete insulin therapy system 1003 can then be sent from the translation service 1011 to a user device 1008 of the user. The translated therapy parameters for the discrete insulin therapy system 1003 can include recommended settings for the discrete insulin therapy system 1003. Although not illustrated in FIG. 14, in some cases, the discrete insulin therapy system 1003 can be configured according to the translated therapy parameters and/or recommended settings. For instance, the settings can be applied at a controller of the discrete insulin therapy system 1003 to control insulin delivery by the discrete insulin therapy system 1003 (e.g., to prepare a particular number of insulin units or a bolus amount for injection).

Figure 15:
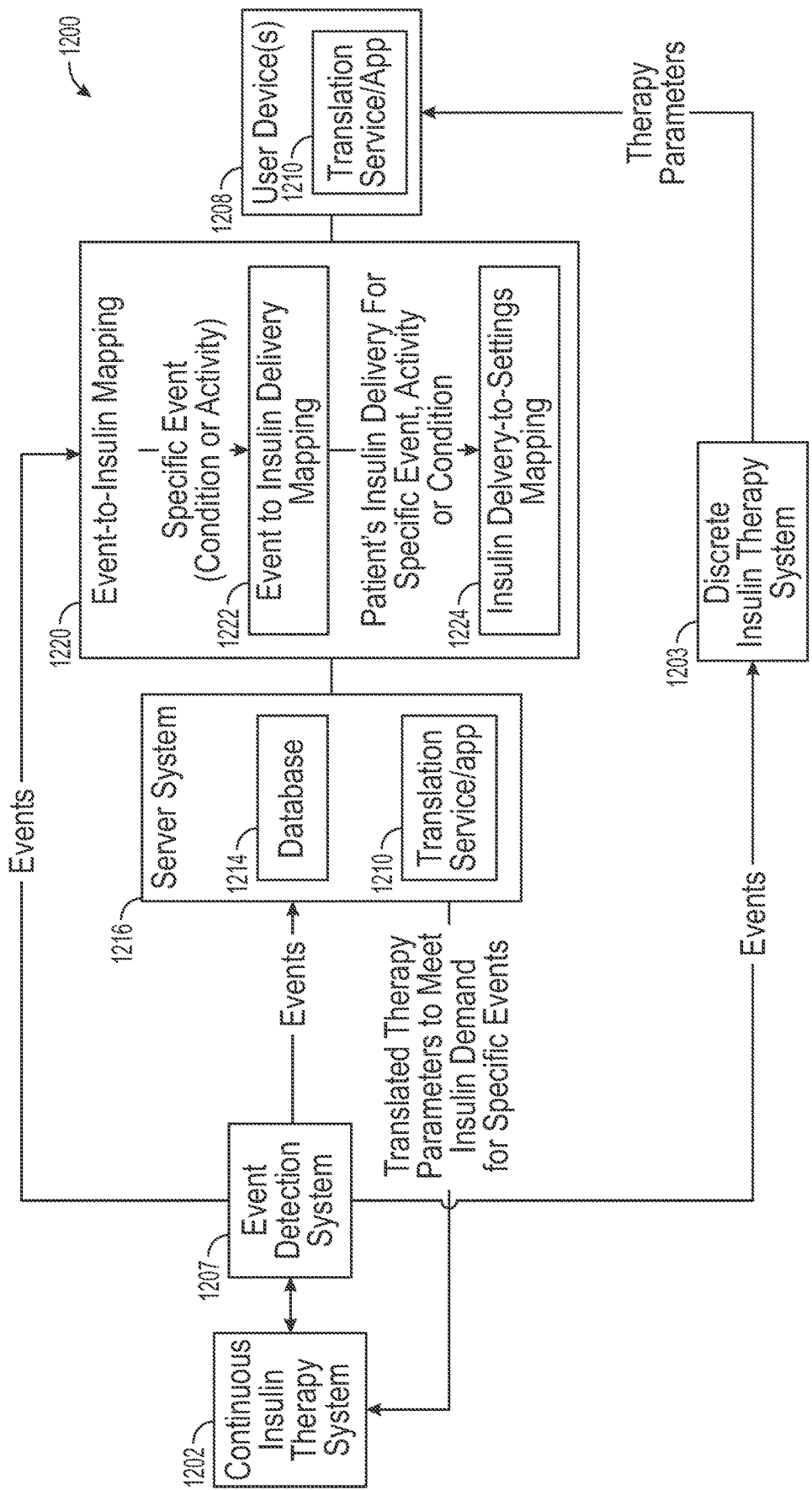
FIG. 15 is a block diagram illustrating a system in accordance with certain embodiments.

FIG. 15 is a block diagram illustrating a system 1200 in accordance with certain embodiments. The system 1200 includes a continuous insulin therapy system 1202, an event detection system 1207, an event-to-insulin mapping service 1220, a server system 1216 including a parameter translation service (or app) 1211 and a database 1214, a user device 1008, and a discrete insulin therapy system 1203. The parameter translation service (or app) 1211 can be used for translating therapy parameters of the discrete insulin therapy system 1203 to translated therapy parameters for use at the continuous insulin therapy system 1202. Example embodiments of the continuous insulin therapy system 1202, the discrete insulin therapy system 1203, and the event detection system 1207, the server system 1216, and the event-to-insulin mapping service 1220 are described above with reference to FIGS. 10 and 13, and for sake of brevity, the description of those systems will not be repeated.

The discrete insulin therapy system 1203 can provide therapy parameters including sensor data and insulin data settings for the discrete insulin therapy system 703, and control algorithms implemented by the discrete insulin therapy system 703 to the event-to-insulin mapping service 1220. The insulin data can include information that describes a user's insulin demand during different time periods. Depending on the implementation, the event-to-insulin mapping service 1220 can be implemented at a server system 1216, at the user device 1208 or at the discrete insulin therapy system 1203, and therefore is illustrated as a separate block 1220 to account for any of those implementations.

The event detection system 1207 can detect various events associated with a user. An event can be a specific condition or activity that is indicative of a physical behavior of the user. Each event can potentially impact physiological glucose dynamics of the user and can be correlated to a change in an insulin demand of the user and/or blood glucose levels of the user. Non-limiting examples of events can include, but are not limited to meal ingestion events, sleep or resting events, physical activity events, an exercise events and work-related events. Information about each event and the timing thereof can be provided to the continuous insulin therapy system 1202, the server system 1216, the user device 1208, the discrete insulin therapy system 1203, and to the event-to-insulin mapping service 1220.

In response to each event that is detected, the event-to-insulin mapping service 1220 can determine an insulin delivery profile for the discrete insulin therapy system 1203 during a period following the event. The insulin delivery profile comprises therapy parameters for the discrete insulin therapy system 1203 to provide insulin delivery in accordance with the insulin delivery profile during the period following the event. The therapy parameters can include therapy settings for insulin delivery to meet insulin demand in response to the specific event (e.g., condition or activity). Non-limiting examples of the therapy parameters can include, but are not limited to: a total daily dosage of insulin; type, dosage and timing of long-lasting insulin to be injected in response to the event as determined based on the basal profile; type, dosage and timing of rapid acting insulin to be injected in response to the event (as determined based on the bolus data to meet insulin demand for the event); the active insulin time; the insulin sensitivity factor; the carbohydrate-to-insulin ratio, etc.

The event-to-insulin mapping service 1220 can map the detected event to the insulin delivery profile. The event-to-insulin mapping service 1220 can then map therapy parameters to translated therapy parameters for the continuous insulin therapy system 1202. Non-limiting examples of the translated therapy parameters can include, but are not limited to: a basal profile comprising basal rate parameters and type and dosage of basal insulin; bolus data comprising type, dosage and timing of bolus insulin to meet insulin demand in response to the event; an active insulin time; an insulin sensitivity factor; a carbohydrate-to-insulin ratio, etc. The mapping of the event to the translated therapy parameters can be stored in a database 1214. As will be explained below, when configured and operated in accordance with the translated therapy parameters the continuous insulin therapy system 1202 can provide insulin delivery in accordance with the insulin delivery profile.

When the continuous insulin therapy system 1202, the translation service 1211 at the user device 1208, or the translation service 1211 at the server system 1208 receives an indication that the event is subsequently detected, the translation service 1211 can retrieve the translated therapy parameters for the continuous insulin therapy system 1202 from the database 1214. The translated therapy parameters can be presented via a user interface the user device 1208 and/or the continuous insulin therapy system 1202. The translated therapy parameters for the continuous insulin therapy system 1202 can include recommended settings for the continuous insulin therapy system 1202. In addition, the translated therapy parameters can be applied at the continuous insulin therapy system 1202 to configure it. For example, settings of the continuous insulin therapy system 1202 can be configured in accordance with the translated therapy parameters so that the continuous insulin therapy system 1202 is automatically or manually (e.g., by the user or health care provider) configured according to the translated therapy parameters and/or recommended settings. For instance, the settings can be applied at a controller of the continuous insulin therapy system 1202 to control insulin delivery by the continuous insulin therapy system 1202 (e.g., cause it to deliver insulin to the user and provide insulin delivery in accordance with the insulin delivery profile). This way, an insulin delivery demand associated with that event can be satisfied.

Figure 16:
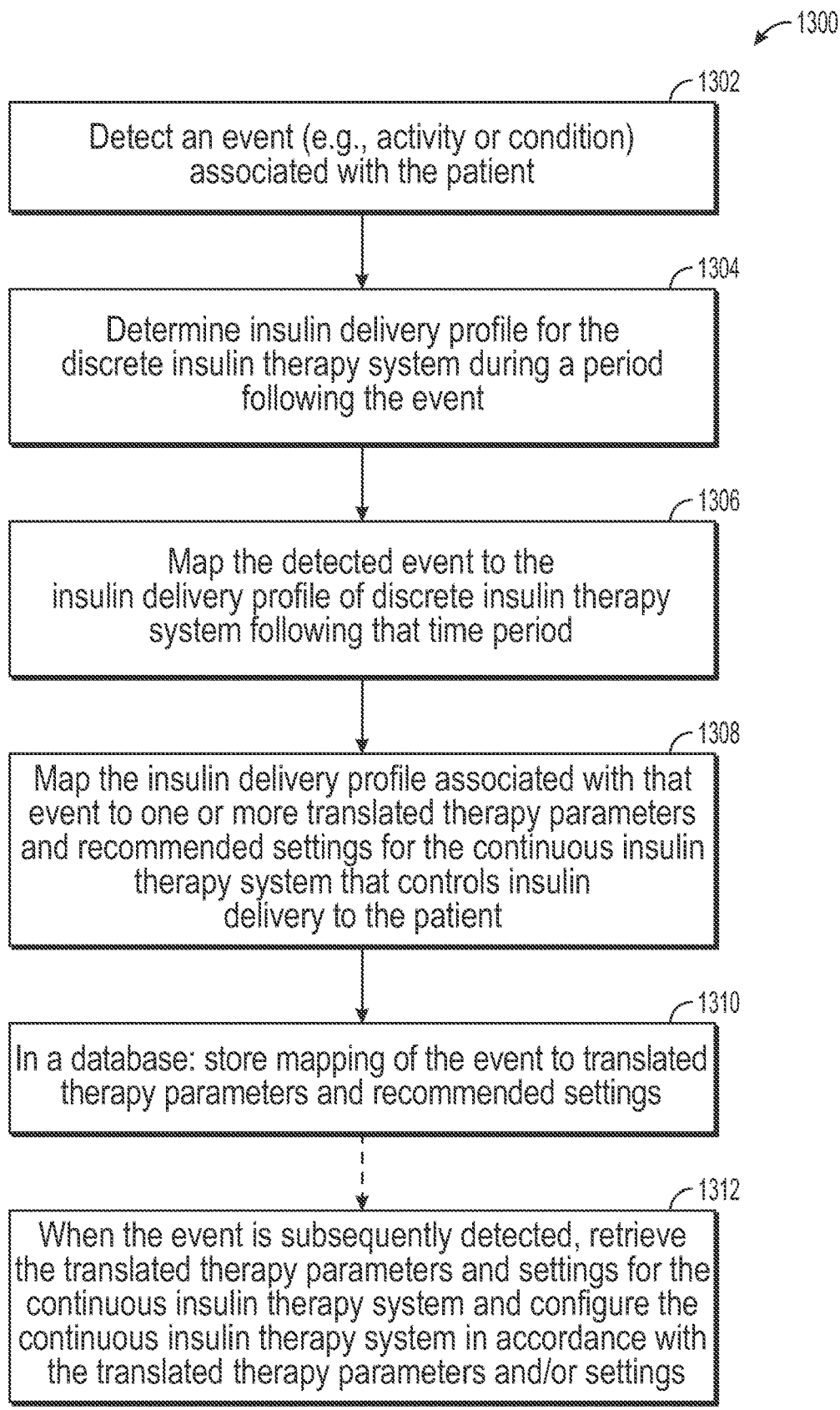
FIG. 16 is a flowchart illustrating a method for translating therapy parameters of a discrete insulin therapy system to translated therapy parameters for use at a continuous insulin therapy system in accordance with certain embodiments.

FIG. 16 is a flowchart illustrating a method 1300 for translating therapy parameters of a discrete insulin therapy system 1203 to translated therapy parameters for use at a continuous insulin therapy system 1202 in accordance with certain embodiments. The user device 1208 regularly logs an insulin delivery profile for the user including therapy parameters for the discrete insulin therapy system 1203. The insulin delivery profile can vary over time. The insulin delivery profile includes therapy parameters that will provide insulin delivery during a period following occurrence of the event. Non-limiting examples of the therapy parameters can include, but are not limited to: a total daily dosage of insulin; type, dosage and timing of long-lasting insulin to be injected in response to the event; type, dosage and timing of rapid acting insulin to meet insulin demand to be injected in response to the event; an active insulin time; an insulin sensitivity factor; a carbohydrate-to-insulin ratio, etc.

The method 1300 starts at 1302, where an event detection system 1207 detects an event associated with a user. At 1304, the translation service 1211 determines an insulin delivery profile for the discrete insulin therapy system 1203 during a period following occurrence of the event. At 1306, the translation service 1211 maps the detected event to the insulin delivery profile. At 1308, the translation service 1211 maps therapy parameters from the insulin delivery profile (that was determined at 1304) to translated therapy parameters for the continuous insulin therapy system 1202. The translated therapy parameters can provide insulin delivery in accordance with the insulin delivery profile and satisfy an insulin delivery demand associated with that event. In other words, the translated therapy parameters, when applied at the continuous insulin therapy system 1202 can configure the continuous insulin therapy system 1202 to deliver insulin to the user in accordance with the insulin delivery profile. Non-limiting examples of the translated therapy parameters can include, but are not limited to, one or more of: a basal profile comprising basal rate parameters and type and dosage of basal insulin as determined based on the type, dosage and timing of long-lasting insulin; bolus data comprising type, dosage and timing of bolus insulin to meet insulin demand in response to the event as determined based on the type, dosage and timing of rapid acting insulin; the active insulin time; the insulin sensitivity factor; and the carbohydrate-to-insulin ratio. At 1310, the mapping of the event to the translated therapy parameters can be stored in a database 1214.

When the event is subsequently detected (at 1312), the translation service 1211 (at server system 1216 or at user device 1208) can retrieve the translated therapy parameters for the continuous insulin therapy system 1202 and provide them to the continuous insulin therapy system 1202 and/or to a user device 1208 of the user, which can in turn provide the translated therapy parameters for the continuous insulin therapy system 1202. The translation service 1211 can retrieve the translated therapy parameters for the continuous insulin therapy system 1202 from the database 1214, for example, when the continuous insulin therapy system 1202, the translation service 1211 at the user device 1208, or the translation service 1211 at the server system 1208 receives an indication that the event is subsequently detected. The translated therapy parameters can be presented via a user interface the user device 1208 and/or the continuous insulin therapy system 1202. The translated therapy parameters for the continuous insulin therapy system 1202 can include recommended settings for the continuous insulin therapy system 1202.

Setting(s) of the continuous insulin therapy system 1202 can then be configured in accordance with the translated therapy parameters, for example, by applying the setting(s) at the continuous insulin therapy system 1202 to configure it and control insulin delivery by the continuous insulin therapy system 1202. For example, settings of the continuous insulin therapy system 1202 can be configured in accordance with the translated therapy parameters so that the continuous insulin therapy system 1202 is automatically or manually configured according to the translated therapy parameters and/or recommended settings. For instance, the settings can be applied at a controller of the continuous insulin therapy system 1202 to control insulin delivery by the continuous insulin therapy system 1202 (e.g., cause it to deliver insulin to the user and provide insulin delivery in accordance with the insulin delivery profile). This way, an insulin delivery demand associated with that event can be satisfied.

The various tasks performed in connection with a process disclosed herein may be performed by software, hardware, firmware, or any combination thereof. It should be appreciated that an embodiment of an illustrated process may include any number of additional or alternative tasks, the tasks shown in the figures need not be performed in the illustrated order, and a disclosed process may be incorporated into a more comprehensive procedure or process having additional functionality not described in detail herein. Moreover, one or more of the tasks shown in a figure could be omitted from an embodiment of the depicted process as long as the intended overall functionality remains intact.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method performed by a translation service hosted at a server system for translating one or more therapy parameters of a first insulin therapy system to one or more translated therapy parameters for use at a second insulin therapy system, the method comprising:
sending a therapy profile generated at the first insulin therapy system to a translation service, the therapy profile comprising one or more therapy parameters;
translating at least one therapy parameter from the therapy profile into at least one translated therapy parameter that is mapped to and adapted for use by the second insulin therapy system that is different than the first insulin therapy system; and
sending the at least one translated therapy parameter to the second insulin therapy system for use at the second insulin therapy system;
wherein:
each of the first insulin therapy system and the second insulin therapy system comprises one of a continuous insulin therapy system or a discrete insulin therapy system, the first and second insulin therapy systems comprising the continuous insulin therapy system and the discrete insulin therapy system;
the continuous insulin therapy system comprises an insulin infusion device that regulates delivery of insulin to a user, and a glucose sensor to provide sensor data that indicates a glucose level of the user; and
the discrete insulin therapy system comprises an insulin injection device that is used to discretely inject insulin.

2. The method according to claim 1, the method further comprising:
generating at least one setting to be applied at the second insulin therapy system based on the at least one translated therapy parameter; and
communicating an instruction to apply the at least one setting to the second insulin therapy system for use at the second insulin therapy system.

3. The method according to claim 2, wherein the first insulin therapy system comprises the continuous insulin therapy system, and wherein the at least one therapy parameter from the therapy profile comprises at least one of:
a basal profile comprising at least one basal rate setting for a user that indicates a rate of continuous insulin infusion delivered to the user;
an active insulin time that indicates an amount of time a bolus of rapid acting insulin remains active in the user after injection;
an insulin sensitivity factor of the user that indicates an amount that blood glucose of the user is reduced by one unit of insulin;
a carbohydrate-to-insulin ratio for the user that indicates a ratio of an amount of carbohydrates in grams covered by one unit of insulin; or
a total daily dose of insulin comprising total basal insulin delivered to the user and total bolus insulin delivered to the user.

4. The method according to claim 3, wherein the second insulin therapy system comprises the discrete insulin therapy system, and wherein the translating comprises:
mapping the at least one basal rate setting for the user to a number of long acting insulin units to be injected by the user and timing recommendations for injection of the long acting insulin units; and
wherein the generating at least one setting to be applied at the second insulin therapy system, comprises:
adjusting the number of long acting insulin units to be injected by the user and the timing recommendations for injection of the long acting insulin units.

5. The method according to claim 3, wherein the second insulin therapy system comprises the discrete insulin therapy system, and wherein the translating comprises:
mapping the insulin sensitivity factor of the user to a number of rapid acting insulin units to be injected by the user during periods of elevated glucose; and
wherein the generating at least one setting to be applied at the second insulin therapy system, comprises:
adjusting rapid dosing parameters by setting: the number of rapid acting insulin units to be injected by the user during periods of elevated glucose.

6. The method according to claim 3, wherein the second insulin therapy system comprises the discrete insulin therapy system, and wherein the translating comprises:
mapping the carbohydrate-to-insulin ratio for the user to a number of rapid acting insulin units to be injected by the user before consuming a particular amount of carbohydrates; and
wherein the generating at least one setting to be applied at the second insulin therapy system, comprises:
adjusting rapid dosing parameters by setting: the number of rapid acting insulin units to be injected by the user before consuming a particular amount of carbohydrates.

7. The method according to claim 2, wherein the first insulin therapy system comprises the discrete insulin therapy system, and wherein the at least one therapy parameter from the therapy profile comprises at least one of:
a number of long acting insulin units to be injected by the user and timing recommendations for injection of the long acting insulin units;
a number of rapid acting insulin units to be injected by the user during periods of elevated glucose;
another number of rapid acting insulin units to be injected by the user before consuming a particular amount of carbohydrates;
an active insulin time that indicates an amount of time the rapid acting insulin remains active in the user after injection;
an insulin sensitivity factor of the user that indicates an amount that blood glucose of the user is reduced by one unit of insulin;
a carbohydrate-to-insulin ratio for the user that indicates a ratio of an amount of carbohydrates in grams covered by one unit of insulin; or
a total daily dose of insulin delivered to the user.

8. The method according to claim 7, wherein the second insulin therapy system comprises the continuous insulin therapy system, and wherein the translating comprises:
mapping the number of long acting insulin units and the timing recommendations for injection to a basal profile comprising at least one basal rate setting for the user that indicates a rate of continuous insulin infusion delivered to the user.

9. The method according to claim 7, wherein the second insulin therapy system comprises the continuous insulin therapy system, and wherein the translating comprises:
mapping the number of rapid acting insulin units to be injected by the user during periods of elevated glucose to an insulin sensitivity factor of the user that indicates an amount that blood glucose of the user is reduced by one unit of insulin.

10. The method according to claim 7, wherein the second insulin therapy system comprises the continuous insulin therapy system, and wherein the translating comprises:
mapping the number of rapid acting insulin units to be injected by the user before consuming a particular amount of carbohydrates to a carbohydrate-to-insulin ratio for the user that indicates a ratio of an amount of carbohydrates in grams covered by one unit of insulin.

11. At least one non-transitory computer-readable medium having program code instructions stored thereon that are configurable to cause at least one processor to perform a method for translating one or more therapy parameters of a first insulin therapy system to one or more translated therapy parameters for use at a second insulin therapy system, the method comprising:
receiving a therapy profile at a translation service, wherein the therapy profile was generated at the first insulin therapy system comprises one or more therapy parameters;
translating at least one therapy parameter from the therapy profile into at least one translated therapy parameter that is mapped to and adapted for use by the second insulin therapy system that is different than the first insulin therapy system; and
sending the at least one translated therapy parameter to the second insulin therapy system for use at the second insulin therapy system;
wherein:
each of the first insulin therapy system and the second insulin therapy system comprises one of a continuous insulin therapy system or a discrete insulin therapy system, the first and second insulin therapy systems comprising the continuous insulin therapy system and the discrete insulin therapy system;

the continuous insulin therapy system comprises an insulin infusion device that regulates delivery of insulin to a user, and a glucose sensor to provide sensor data that indicates a glucose level of the user; and the discrete insulin therapy system comprises an insulin injection device that is used to discretely inject insulin.

12. The at least one non-transitory computer-readable medium according to claim 11, wherein sending comprises:
generating at least one setting to be applied at the second insulin therapy system based on the at least one translated therapy parameter; and
communicating an instruction to apply the at least one setting to the second insulin therapy system for use at the second insulin therapy system.

13. The at least one non-transitory computer-readable medium according to claim 12, wherein the first insulin therapy system comprises the continuous insulin therapy system, and wherein the at least one therapy parameter from the therapy profile comprises at least one of:
a basal profile comprising at least one basal rate setting for a user that indicates a rate of continuous insulin infusion delivered to the user;
an active insulin time that indicates an amount of time a bolus of rapid acting insulin remains active in the user after injection;
an insulin sensitivity factor of the user that indicates an amount that blood glucose of the user is reduced by one unit of insulin;
a carbohydrate-to-insulin ratio for the user that indicates a ratio of an amount of carbohydrates in grams covered by one unit of insulin; or
a total daily dose of insulin comprising total basal insulin delivered to the user and total bolus insulin delivered to the user.

14. The at least one non-transitory computer-readable medium according to claim 13, wherein the second insulin therapy system comprises the discrete insulin therapy system, and wherein the translating comprises:
mapping the at least one basal rate setting for the user to a number of long acting insulin units to be injected by the user and timing recommendations for injection of the long acting insulin units; and
wherein generating at least one setting to be applied at the second insulin therapy system, comprises:
adjusting the number of long acting insulin units to be injected by the user and timing recommendations for injection of the long acting insulin units.

15. The at least one non-transitory computer-readable medium according to claim 13, wherein the second insulin therapy system comprises the discrete insulin therapy system, and wherein translating comprises:
mapping the insulin sensitivity factor of the user for the user to a number of rapid acting insulin units to be injected by the user during periods of elevated glucose; and
wherein the generating at least one setting to be applied at the second insulin therapy system, comprises:
adjusting rapid dosing parameters by setting: the number of rapid acting insulin units to be injected by the user during periods of elevated glucose.

16. The at least one non-transitory computer-readable medium according to claim 13, wherein the second insulin therapy system comprises the discrete insulin therapy system, and wherein translating comprises:
mapping the carbohydrate-to-insulin ratio for the user to a number of rapid acting insulin units to be injected by the user before consuming a particular amount of carbohydrates; and
wherein the generating at least one setting to be applied at the second insulin therapy system, comprises:
adjusting rapid dosing parameters by setting: the number of rapid acting insulin units to be injected by the user before consuming a particular amount of carbohydrates.

17. A system for translating one or more therapy parameters of a first insulin therapy system to one or more translated therapy parameters for use at a second insulin therapy system, the system comprising:
at least one hardware processor configurable by machine-readable instructions to:
receive a therapy profile, wherein the therapy profile was generated at the first insulin therapy system and comprises one or more therapy parameters;
translate at least one therapy parameter from the therapy profile into at least one translated therapy parameter that is mapped to and adapted for use by the second insulin therapy system that is different than the first insulin therapy system; and
send the at least one translated therapy parameter to the second insulin therapy system for use at the second insulin therapy system;
wherein:
each of the first insulin therapy system and the second insulin therapy system comprises one of a continuous insulin therapy system or a discrete insulin therapy system, the first and second insulin therapy systems comprising the continuous insulin therapy system and the discrete insulin therapy system;
the continuous insulin therapy system comprises an insulin infusion device that regulates delivery of insulin to a user, and a glucose sensor to provide sensor data that indicates a glucose level of the user; and
the discrete insulin therapy system comprises an insulin injection device that is used to discretely inject insulin.

18. The system according to claim 17, wherein the second insulin therapy system comprises: a controller, and wherein the at least one hardware processor is further configurable by machine-readable instructions to:
generate at least one setting to be applied at the second insulin therapy system based on the at least one translated therapy parameter; and
communicate an instruction to apply the at least one setting to the second insulin therapy system for use at the second insulin therapy system.

19. The system according to claim 18, wherein the first insulin therapy system comprises the continuous insulin therapy system, and wherein the at least one therapy parameter from the therapy profile comprises at least one of:
a basal profile comprising at least one basal rate setting for a user that indicates a rate of continuous insulin infusion delivered to the user;
an active insulin time that indicates an amount of time a bolus of rapid acting insulin remains active in the user after injection;
an insulin sensitivity factor of the user that indicates an amount that blood glucose of the user is reduced by one unit of insulin;

a carbohydrate-to-insulin ratio for the user that indicates a ratio of an amount of carbohydrates in grams covered by one unit of insulin; or a total daily dose of insulin comprising total basal insulin delivered to the user and total bolus insulin delivered to the user.

20. The system according to claim 19, wherein the second insulin therapy system comprises the discrete insulin therapy system, and wherein the at least one hardware processor is configurable by machine-readable instructions to:

map the at least one basal rate setting for the user to a number of long acting insulin units to be injected by the user and timing recommendations for injection of the long acting insulin units; and wherein the at least one setting to be applied at the second insulin therapy system comprises: the number of long acting insulin units to be injected by the user and timing recommendations for injection of the long acting insulin units.

21. The system according to claim 19, wherein the second insulin therapy system comprises the discrete insulin therapy system, and wherein the at least one hardware processor is configurable by machine-readable instructions to: map the insulin sensitivity factor of the user to a number of rapid acting insulin units to be injected by the user during periods of elevated glucose; and wherein the at least one setting to be applied at the second insulin therapy system, comprises: the number of rapid acting insulin units to be injected by the user during the periods of elevated glucose.

22. The system according to claim 19, wherein the second insulin therapy system comprises the discrete insulin therapy system, and wherein the at least one hardware processor is configurable by machine-readable instructions to: map the carbohydrate-to-insulin ratio for the user to a number of rapid acting insulin units to be injected by the user before consuming a particular amount of carbohydrates; and wherein the at least one setting to be applied at the second insulin therapy system, comprises: the number of rapid acting insulin units to be injected by the user before consuming the particular amount of carbohydrates.

* * * * *